United States Patent [19]
Bohr et al.

[11] Patent Number: 6,060,293
[45] Date of Patent: May 9, 2000

[54] RESONANCE DRIVEN CHANGES IN CHAIN MOLECULE STRUCTURE

[75] Inventors: Jakob Bohr, Humlebæk; Henrik Georg Bohr, Holte; Søren Brunak, Frederiksberg C, all of Denmark

[73] Assignee: ProKyon ApS, Copenhagen K, Denmark

[21] Appl. No.: 08/930,452

[22] PCT Filed: Apr. 1, 1996

[86] PCT No.: PCT/DK96/00158

§ 371 Date: Nov. 26, 1997

§ 102(e) Date: Nov. 26, 1997

[87] PCT Pub. No.: WO96/30394

PCT Pub. Date: Oct. 3, 1996

[30] Foreign Application Priority Data

Mar. 31, 1995 [DK] Denmark ................................ 0361/95

[51] Int. Cl.[7] .................................................. C12N 13/00
[52] U.S. Cl. ........................................................ 435/173.1
[58] Field of Search ........................................... 435/173.1

[56] References Cited

U.S. PATENT DOCUMENTS 4,678,553  7/1987  Mandle et al. ........................... 204/522

OTHER PUBLICATIONS

Bohr, et al., Resonator Driven Protein Folding: The Implication of Topology for Protein Structure and Folding, Protein Folds (A Distance–Based Approach), 2nd, CRC, Boca Raton, Florida, Meeting date 1994, pp. 243–252 (1996).

Bohr et al., "The Formation of Protein Structure", Europhys. News, 27(2), pp. 50–54, 1996.

Bohr et al., "Protein Folding and Wring Resonaces", Biophysical J., 70(2), part 2, p. A148, Abstract M–PM–C9, Feb. 1996.

Bohr et al., "Coherent Topological Phenomena in Protein Folding", Folding Des., 2(3), pp. S15–S18, 1997.

Bohr et al., "Protein Folding and Wring Resonances", Biophysical J., 63 (2–3), pp. 97–105, 1997.

King, J., Chem. Eng. News, Apr. 10, 1989, "Deciphering the Rules of Protein Folding", pp. 32–54.

Borman, S. Chem. Eng. News, May 27, 1996, 74(22), "Scientists Refine Understanding of Protein Folding and Design, Protein Conference Covers Folding, Chaperones, Design and Modification, Therapeutics, Theory and Structure Prediction", pp. 29.

*Primary Examiner*—Jon P. Weber
*Attorney, Agent, or Firm*—Iver P. Cooper

[57] ABSTRACT

The invention relates to the technical application of electromagnetic radiation such as microwaves and radiowaves and application of ultra sound to chain molecules. In particular, the present invention relates to the utilization of topological excitations such as wring, twist and torsional modes, e.g., for generating structure, such as in folding, refolding or renaturation, and denaturation or unfolding of peptides, polypeptides, proteins, and enzymes; for generating changes in molecular affinity; for stimulating drug receptor interactions; and for changing molecular communication, is described. The technique is based on a new understanding of the underlying physical phenomenon and can also be applied to other chain molecules and biologically active biomolecules and tailored polymers such as glucoproteins, antibodies, genomic chain molecules such as DNA and RNA as well as PNA, carbohydrates, and synthetic and natural organic polymers. The invention is especially applicable for solving problems related to inclusion bodies and aggregation when using recombinant DNA and protein engineering techniques. Furthermore, the invention can be utilized in therapeutic treatment and in development and production of pharmaceuticals. The area of applicability ranges from biotechnological industry, food industry, drug industry, pharmacological industry, chemical industry, and concerns, e.g., the treatment of conditions and diseases related to influenza, hepatitis, polio, malaria, borrelia, diabetes, Alzheimer's disease, Creutzfeldt Jakob disease, other prion related diseases, multiple sclerosis, cataract, heart diseases, cancer, and aging.

33 Claims, No Drawings

RESONANCE DRIVEN CHANGES IN CHAIN MOLECULE STRUCTURE

FIELD OF THE INVENTION

This invention relates to a technology for changing the three-dimensional structure of chain molecules, especially to the folding and refolding of proteins and nucleic acids in vitro as well as in vivo. This invention also relates to changing the dynamic wring state of a chain molecule, with or without changing its three-dimensional structure. This invention further relates to production and purification of chain molecules, for example in connection with genetically engineered eukaryotic proteins in prokaryotic cells, e.g. for drug development. Furthermore the invention relates to improvements in detection of bio-molecular structures and for therapeutic treatment of various diseases and conditions.

GENERAL BACKGROUND OF THE INVENTION

Over the last decades there has been an increasing interest in understanding the mechanism of changing the three-dimensional structure of macro-molecules, in particular the mechanism for folding proteins in solution and coiling polynucleic acids and analogues thereof. Also, efforts have been made in order to predict or calculate the preferred three-dimensional structure of proteins.

Predictions of the protein secondary structure can be obtained by data driven methods, such as artificial neural network algorithms trained on structural data from the Brookhaven Protein Data Bank. These methods are able to classify up to about approximately 75% of the amino acid residues correctly in a three state prediction: α-helix, β-sheet, or coil. Earlier statistical methods such as the Chou-Fasmann prediction scheme have lower performance. Alternatively, structural insight can be obtained from homologous proteins using homology modelling. When sufficiently large sequence similarity between two amino acid sequences is present (more than about 25%), it is in most cases possible to build a good model of one protein by analyzing the structure of the other. This method is ineffective when homologous proteins with known structure are unavailable in the databases. Simulation of protein folding based on molecular dynamics algorithms is yet another option to study structure. Due to the computational complexity of this task, molecular dynamics is normally feasible only in constrained versions, where most of the degrees of freedom in the problem are removed.

Until now there has not been established a universal theory for folding of proteins, which fully explains the transition from the unfolded polypeptide chain to the folded protein. Especially, the understanding of the initialization of the transition is crucial when attempts are made to control the folding process. Many proteins fold in less than a second, a time period in which a polypeptide would only be able to scan (visit) a very small fraction of the possible conformations. Consequently, there is no reason to believe that protein folding is based on a trial-and-error protocol. What up to now has been lacking is the understanding of the mechanism which brings the protein across many barriers and leads it towards the folded state. Though some proteins are able to refold in a test tube, cellular factors and cellular conditions are important for the initial folding of proteins. One indication of this comes from biotechnology, where high levels of expression of proteins by recombinant DNA are often obtained, but at the same time much of the resultant material does not fold to its native soluble conformation, but is found as macroscopic insoluble aggregates, or inclusion bodies.

DESCRIPTION OF THE INVENTION

Now, the present inventors have found reason to believe that the transformation of a chain molecule from an unfolded state to a folded state is due to excitations of a collective twist mode of the backbone of said chain molecule. By introducing this new theory for the folding of chain molecules, a number of features of the folding processes can be predicted and controlled. The theory and its application were primarily developed for proteins, but can be easily extended to other chain molecules, such as nucleic acid, synthetic organic polymers, etc.

Furthermore, a number of problems, e.g. appearing when proteins fail to fold, can in many cases be explained. By using this theory, it is also possible to give guidelines for the solution of such problems, and to solve the problems. Experimental work (see the Experimental Section) has supported the theory and applicability of the guidelines. Thus, aspects of the present invention relate to methods for solving such problems and to methods for treating chain molecules in order to obtain highly purified and active products from natural as well as tailored chain molecules. Below is given examples of such problems that can arise when handling and manipulating chain molecules, the solution of such problems being aspects of the present invention.

(a) Problems with the folding of proteins in a given solution, at a given concentration and at a given temperature.

(b) Problems with folding of well known proteins in non-native environments, e.g., problems with folding after the synthesis of human proteins in micro-organisms such as *E.coli*.

(c) Problems with the misfolding of proteins in solution.

(d) Purification problems (e.g. aggregation and formation of inclusion bodies) in industrial production of engineered protein products.

Other aspects of the invention, useful, e.g., in medicine, are related to regulation and control of biological processes by controlling the three-dimensional structure of molecules involved in the processes, either in the direction towards a structure having a desired functionality, or in the direction away from a structure having an undesired or adverse functionality.

The method according to the invention is based on the discovery of specific collective twist modes of the backbone of chain molecules.

The backbone of natural chain molecules comprises segments representing a part of Nature's wide variety of available building blocks, e.g. amino acids (in proteins such as enzymes), carbohydrates (in poly-saccharides such as cellulose) and nucleotides (in genomic systems such as DNA). In contrast to the simplicity of the primary structure of such chain molecules, the three-dimensional structure represents a high degree of complexity.

In the present context, the term "chain molecule" is intended to mean molecules consisting of a plurality of consecutive monomer fragments optionally carrying one or more substituents. In many important types of chain molecules, the monomer fragments are substantially identical along the chain, such as discussed below. While most types of chain molecules can easily be divided into "proper" monomer fragments from which the molecule can be considered built up with reference to a particular chemical or biological reaction such as condensation (and into which it can, in many cases, decompose), also "inherent" chain molecules, such as hydrocarbons, e.g., n-decane, exist which are normally not visualized as consisting of monomer fragments; for the purpose of the present description and claims, the monomers of such "inherent" chain molecules are considered to be the smallest possible "building stone", in the case of n-decane, thus, methylene. The chain of the chain molecule will normally comprise at least 4 monomers, provided, however, that the backbone of the chain comprises at least 10 atoms; more commonly, the chain of the chain molecule will comprise at least 10 monomers, and in many of the most important cases at least 20 monomers, such as 50 monomers. In most cases, the monomer fragments are identical or substantially identical, although it is evidently within the scope of the present invention to change the functionality of the three-dimensional structure of chain molecules which do not conform to this criterion.

Examples of such chain molecules are natural proteins including polypeptides, glycoproteins, lipoproteins, enzymes, antibodies, and proteins with prosthetic groups; tailored proteins; genomic chain molecules including RNA and DNA; artificial genomic chain molecules including PNA; carbohydrates including polysaccharides; and synthetic organic polymers; among which proteins, tailored proteins, and antibodies, e.g. antibodies produced by cloning are preferred examples. (in vivo production of antibodies may be enhanced by excitation of a collective twist mode of the backbone of the antibodies.) In the case of proteins the monomer fragment is a —NH—$CH_2$—CO— unit, corresponding to a glycinyl moiety. Generally, the term "monomer fragment" is used for the repeating unit of the backbone of the chain molecule. The monomer fragments may optionally be substituted with aliphatic and/or groups. For proteins the monomer fragment is a glycinyl moiety often substituted with groups corresponding to the side chains of the natural amino acids. For poly-nucleic acid. such as RNA and DNA, the monomers are nucleotides consisting of three parts: the five carbon sugar, e.g. deoxyribose or ribose, one or more phosphates attached to the 5' position of the sugar, and the organic heteroaromatic base attached to the 1' position of the sugar. The monomer fragment in the latter case is the sugar combined with the phosphate(s).

In the present context, the term "tailored proteins" is intended to mean either a de novo designed protein or an existing protein which has been re-designed, in both cases to obtain a desired function.

In special cases, the backbone of a chain molecule can form a closed curve. One well known example is circular DNA. Also, two or more chain molecules may be chemically bonded to each other. In such a case, one individual chain molecule can be considered to be a substituent on another chain molecule and vice versa.

In the case of proteins, after the bio-synthesis in their natural environment (i.e. the cell), the polypeptide chains fold to one unique three-dimensional structure apart form conformational sub-states. In contrast to this, folding and refolding in vitro often leads to incomplete folding and/or misfolding. In many cases this mishap can be due to unwanted aggregation of the unfolded chains or can be due to the lack of propeptides and signal peptides that were present in the natural cellular environment, but were cleaved off during or after the folding process. In some cases chaperones also play an important role. However, the theory of the inventors points to the intriguing possibility that the "resonance frequency" is specific to the cell in which the protein synthesis takes place. This could be the main origin of the problems mentioned in (b) and (d) above.

Thus, one aspect of the present invention provides a method for changing the functionality of the three-dimensional structure of one or more chain molecules each having a one-dimensional primary structure comprising a backbone the predominant number of bonds of which are non-coaxial or rotationally non-symmetrical, or of aggregates of such molecules, the method comprising applying energy from a high frequency energy source to a fluid system containing such chain molecules under conditions with respect to parameters involving wavelength, amplitude and duration which will initiate a change of the three-dimensional structure to result in a functionality of the three-dimensional structure which is different from the starting functionality of the three-dimensional structure, provided that substantially no decomposition of the backbone of said chain molecule is caused by the application of the high frequency energy.

Another aspect of the present invention provides a method for changing the functionality of the three-dimensional structure of one or more chain molecules contained in a fluid system, each molecule having a one-dimensional primary structure comprising a backbone the predominant bonds of which are non-coaxial or rotational non-symmetrical, or of aggregates of such molecules, the method comprising applying energy to a twist mode of the chain molecules by means of a molecular resonator system not native to the fluid system and thereby initiating a structural change to result in a functionality of the three-dimensional structure which is different from the starting functionality of the three-dimensional structure.

The term "non-coaxial" is used in its normal meaning and indicates that the backbone does not belong to coaxial chains, examples of which are polyyne chains.

The term "rotationally non-symmetric bond" is intended to mean a bond which does not display rotational symmetry.

In the present context, "aggregate of chain molecules" is intended to mean a cluster of at least two chain molecules mutually bonded or interacting often by ionic bonds, hydrogen bonds, and/or van der Waals forces. In the case of aggregates of polypeptides or proteins the individual chain molecules of the cluster may also be linked together by one or more easily reducible sulphur bridges (—S—S—).

Examples of such aggregates of chain molecules are oligomers of chain molecules including homo-oligomers and hetero-oligomers; protein/receptor systems including antibody/antigen complexes, protein/ligand complexes, and docking aggregates; inclusion bodies; and membranes consisting of chain molecules or oligomers thereof, in an interesting embodiment the aggregate is an inclusion body or a antibody/antigen complex.

The term "fluid system" indicates a system in which the chain molecules are in contact with or surrounded by a fluid which permits the change of the three-dimensional structure, such as a liquid (including a liquified gas) or a gas or a lipid environment such as the environment prevailing in a cell membrane. It should be understood that the term "surrounded by" does not rule out the possibility of the chain molecules being attached to a carrier at one site of the molecule. Examples of fluid systems include the prominent example of aqueous systems, including aqueous solutions and suspensions, but also biological systems such as bacterial cells (the interior of which is an aqueous system and the membrane of which is a lipid environment).

Thus, in one interesting embodiment of the present invention the fluid system is a micro-organism. The fluid system may also be represented by the extracellular environment of a fermentation mixture which further comprises a protein producing micro-organism. In both cases the microorganism may be modified in order to produce a non-native protein or a non-native molecular resonator.

The term "molecular resonator system" is intended to mean one or more molecules comprising one or more resonator groups which can couple an eigen mode of the molecular system with a collective twist mode of a chain molecule. Thus, the molecular resonator system is able to deliver high frequency energy to the collective twist mode of a chain molecule. A molecular resonator system should also have a chemical structure that gives it a high degree of affinity to the chain molecule. The eigen mode of the molecular resonator is typically a vibrational, rotational, or quantum mechanical state. It is the existence of long-ranged collective modes, such as twistons, in chain molecules that makes it possible for the molecular resonators to have a relatively long-ranged impact. A detailed discussion of the concepts "twiston" and "collective twist mode" is given in the following.

As will be explained in detail in the following, the high frequency energy can be applied in various ways, in particular by applying microwave energy in a selected (narrow) frequency range, by applying energy from a mechanical resonator such as a piezoelectrical crystal (external resonator), or by using a molecular resonator system (internal resonator). In the latter case the high frequency energy is applied directly to the chain molecule rather than to the fluid system. This interesting case is discussed in detail further below.

As will be described in details in the following, an external resonator system may be used alone or in combination with an molecular resonator system (internal resonator). Also it may be preferred to use an molecular resonator system alone.

The term "functionality" is intended to indicate at least one function (such as a physical and/or chemical and/or biological function) which is related at least in part to the three-dimensional structure of the chain molecule.

The term "decomposition", as used in connection with the backbone, indicates chemical decomposition, normally to break covalent bonds (e.g. hydrolysis) resulting in the reduction of the number of consecutive monomers or atoms in the backbone.

While the application of high frequency energy to the fluid system is primarily intended to cause a change in the functionality of the three-dimensional structure of one or more chain molecules, the possibility of a alteration (increase) of the temperature of the fluid system cannot be excluded. When a certain temperature or temperature range different from the ambient temperature is preferred for performing the method, this temperature can be obtained by heating or cooling using conventional means for cooling and heating. Heating of the fluid system comprising the chain molecule(s) can, e.g., be performed by using conventional heating means including a commercially available microwave oven. It is, however, in most cases preferred that the temperature is controlled by using a thermobath. Thus, it is envisaged that the application of high frequency energy can be applied at a large temperature interval, such as from around −200° C. to around 100° C. The lowest relevant temperature is normally defined by the fluid system containing the chain molecule, but as the use of a liquified gas phase fluid system is within the scope of the present invention, the lower limit is not limited to −200° C. In some cases, e.g. when the chain molecule is in a liquified gas phase or in non-aqueous solvents, it is preferred to perform the application of high frequency energy at a temperature below 0° C., e.g. below −20° C., such as below −70° C. or even below −190° C. The highest relevant temperature is normally defined by the conditions under which the chain molecule decomposes, and therefore, the temperature of the fluid system is normally adjusted to a temperature well below the decomposition temperature for the chain molecule under the given condition with respect to pH, concentration of species other than the chain molecule in question, etc. However, decomposition is often caused by a solvent and/or other species comprised in the fluid system and therefore, in the case where the fluid system is a inert gas phase system, the temperature of the fluid system is in no way limited to 100° C. It is, however, preferred that the temperature increase due to the application of the high frequency energy which is intended to achieve the functional change of the three-dimensional structure is lower than 10° C., e.g. lower than 5° C., such as lower than 3° C., when the temperature of the fluid system is in the range where decomposition of the chain molecule takes place, which may be at a temperature higher than 35° C., such as higher than 40° C., for many relevant chain molecules higher than 50° C., and in some cases higher than 60° C., such as higher than 80° C., or even higher than 100° C.

When using the above-mentioned directions no decomposition, or at least substantially no decomposition, of the backbone of the chain molecule is caused by the application of high frequency energy.

In the present context, the terms "twiston", "wringon", and "collective twist mode" all refer to a topological excitation (collective) of the chain similar to the phenomenon of a phonon (a vibrational mode in a crystal lattice which involves a collective pattern of displacement amplitudes) in crystals, but which involves twist amplitudes instead of displacement amplitudes (see also the Theoretical Section). Chain molecules comprise at least one collective twist mode, but when more than one collective twist mode is present excitation of each of these will normally result in at least slightly different resulting three-dimensional structures.

In the context of twistons, wringons, and collective twist modes the terms "eigenfrequency" and "resonance frequency" refer to the frequency of a standing twist pattern of the backbone. The eigenfrequency is depending on the length and moment of inertia of the chain molecule and is estimated below (see the Theoretical Section).

By the application of high frequency energy to the fluid system containing the chain molecule or directly to the chain molecule, a high frequency mode, such as a collective twist mode, in the backbone of the chain molecule is induced. The frequency of the energy is preferably in a range where a collective twist mode can be excited, especially at a frequency at which resonance of a collective twist mode can be obtained. In order to induce a collective twist mode effectively, and thereby avoid side effects such as heating of the fluid system, the frequency spectrum of the energy source is preferably adapted so that it has components within an interval around the resonance frequency of the collective twist mode. Normally, the relevant interval around the resonance frequency is at least around three times the full width at half maximum of the resonance, such as ten times the full width at half maximum of the resonance. In relation to the frequency of the resonance the frequency of the applied energy is normally from $\frac{1}{10}$ to 10 times the resonance frequency of the twist mode. However, in most cases, especially where the resonance frequency of the twiston is identified, it is preferred to apply the high frequency energy in a narrow frequency band. In certain cases, when unfolding an already folded or aggregated polypeptide or protein, the effect may be obtained, and even maximized, when using a frequency off the resonance of the polypeptide or protein.

For polypeptides and proteins having a length of about 100 amino acids, a rough estimate of the resonance frequency gives around 2.6 GHz (see Theoretical Section). Usually, this estimate is useful for determining the starting conditions for the method according to the invention; below is described how the conditions can be adjusted in accordance with the assessment of the effect of the applied energy. Thus, in order to induce a collective twist mode, the frequency of the applied energy is normally in the range of 0.001 to 1000 GHz, e.g. in the range of 0.01 to 100 GHz, such as in the range of 0.1 to 10 GHz, for example in the range of 0.2 to 5 GHz such as in the range of 0.2 to 0.6 GHz, or in the range 0.6 to 1.0 GHz, or in the range of 1 to 5 GHz.

With respect to the band width of the applied high frequency energy, this is advantageous quite narrow in order to avoid side effects, however, as broad spectrum (mechanical) high frequency devices may be used, a broad frequency range is not prohibitive for obtaining the desired effect. The band width of the applied high frequency energy at half maximum is preferably at the most 0.5 GHz, such as at the most 0.1 GHz or even at the most 10 MHz. For especially target specific applications, e.g. in vivo applications such as the uses related to the treatment of various conditions and diseases, it is preferred that the band width is even narrower, such as at the most 1 MHz, especially at the most 100 kHz, in particular at the most 1 kHz.

The conditions with respect to parameters involving frequency, amplitude, and duration are normally predetermined for a specific chain molecule. The frequency can in most cases be estimated by using the formula (1) in the Theoretical Section. The conditions with respect to amplitude and duration (but also the conditions with respect to fine tuning of the frequency) are normally predetermined by assessment of the effect of the energy involving the parameters on the chain molecule or molecules. This assessment can be performed on the chain molecule or chain molecules while present in a fluid system identical or substantially identical with, or representative for, the fluid system in which the chain molecule or molecules is/are contained during performance of the method according to the invention. Alternatively, the effect of the energy supply under the above-mentioned conditions on the fluid system can be assessed on the fluid system exposed to the energy source, or on at least one sample withdrawn therefrom, by monitoring the effect of the energy supply intermittently or continuously. The application of energy is often adjusted in response to the assessment of the effect. The assessment of the effect of the applied energy can, e.g., be performed by using one or more of the methods or experimental setups described herein. Also, conventional experimental setups normally used to determine the functionalities, such as a physical and/or chemical and/or biological function, of chemical substances, such as chain molecules, may be used.

With respect to the duration of the application of high frequency energy, it is envisaged that application times of from 0.1 ms to several hours, e.g. 8 hours, may be relevant, and in special a constant application over a longer period may be required in order avoid a reversal of the process, e.g., induced by a biological system (see especially the medical application). However, as the process of, e.g., protein folding in it self proceeds with in less than a second it is believed that an application time of from 1 ms to 1 hour, such as from 100 ms to 5 minutes or even from 100 ms to 1 minute, is realistic from most practical applications (longer periods may of course be used). In continuous flow reactors a constant supply of high frequency energy is of course preferred. The application of energy may be performed continuously or intermittently.

It is often preferred that the initial three-dimensional structure of the selected chain molecule is assessed prior to the application of the high frequency energy, and that the fact that the desired change in the three-dimensional structure of said chain molecule has taken place is assessed subsequently.

Thus, e.g., in the case where a sample of a fluid system comprising a protein, e.g. an enzyme, is withdrawn from the system, the increase, or decrease, of the specific enzymatic activity could be used to assess the effect, or lack of effect, of the applied energy, or in the case of a molecular resonator, of the selected molecular resonator system.

Thus, an embodiment of the method for changing the three-dimensional structure of a selected chain molecule comprises:
  applying high frequency energy to the fluid system comprising the selected chain molecule;
  intermittently or continuously monitoring the effect of the applied high frequency energy by monitoring the change in three-dimensional structure of the selected chain molecule;
  optionally adjusting the conditions with respect to parameters involving the amplitude, frequency, and duration of the energy source to enhance said effect.

In an embodiment of the present invention, the desired change in the three-dimensional structure of the chain molecule is assessed by measurement of the biological effect of the chain molecule.

In the case of an enzyme the assessment of the change in the three-dimensional structure of the enzyme may be assessed by measuring the enzymatic activity of said enzyme towards a substrate for said enzyme, and the enzymatic activity can be expressed as the rate of conversion of the substrate for the enzyme to the product of the enzymatic reaction. In this way the effect of the applied high frequency energy can be assessed directly, e.g., by measuring the concentration of the substrate or the product. If any chromophore of the substrate is involved in the enzymatic reaction, the colour change may be a measure for determining the concentration change, and the reaction can the simply be performed in a measuring cell (cuvette) which may be modified in order to apply high frequency energy directly to the reaction mixture. The setup outlined above may be used when the initial three-dimensional structure of the enzyme is an inactive unfolded structure and the resulting three-dimensional structure of the enzyme is an active folded structure (and vice versa).

In the case where the chain molecule is a protein, the assessment of the change in the three-dimensional structure of the protein may be performed by measuring the affinity of said protein for an immobilized ligand for said protein. As an example a standard titer plate or well whereon a ligand for the peptide in question has be immobilized may be used. The result from an experiment where the titer plate is incubated with a solution of the protein in question may be compared with a corresponding experiment where high frequency energy is applied to the solution with no substantial change of the temperature of the solution. A difference in titer is a result of a high frequency energy induced change in the three-dimensional structure of the protein. In the most interesting instance, the initial three-dimensional structure of the protein is an unfolded structure having lower affinity for the immobilized ligand than the resulting folded three-dimensional structure.

Monitoring the change in the three-dimensional structure of the selected chain molecule may also be performed, e.g., by one or more of the other methods described herein, e.g. by using the viscosity/friction apparatus setup described further below.

Furthermore, the initial three-dimensional structure of the selected chain molecule may be assessed prior to the application of the high frequency energy by one or more of the methods described further below, e.g. by using the viscosity/friction apparatus setup described further below, and assessment of the desired change in the three-dimensional structure of said chain molecule is often verified after the treatment.

Also, the conditions with respect to parameters involving amplitude, frequency, and duration may be predetermined based on previous experiments on the same or similar chain molecules, in fluid systems similar to or corresponding to the fluid system containing the chain molecule in question.

In the present context, the terms "native structure" and "native state" are intended to mean the predominant naturally occurring configuration of the chain molecule in a functional state. In the case of proteins, the native structure is a functional state often just referred to as the folded state. The folded state may be stabilized by intramolecular covalent bonds, such as —S—S— bridges in proteins (e.g. cystine bridges). In the case of unnatural chain molecules, the term "native structure" is intended to mean a folded structure with a desired function or structure.

The term "folded state" is intended to mean the native state and any other configuration of the molecule being stabilized, e.g., covalently (e.g. —S—S— bonds), ionically, by hydrogen bonds and/or by van der Waal forces. The folded state represents an ordered and relatively compact state of the chain molecule. (For natural proteins it is often referred to as the native state (see above) where the molecule attain its chemically and/or biologically active form.) Conformational sub-states, i.e. folded structures the proteins can obtain without unfolding as part of their functional cycle, are also considered as folded states.

Accordingly, the term "unfolded state" is intended to mean a state where each monomer of the chain has few or none intramolecular interactions except from the monomers being connected together through the chain of the molecule.

The term "denatured structure" is intended to mean configurations obtained after treatment of the three-dimensional native structure with chemical components which destabilize the three-dimensional native structure or by altering the temperature of the material containing the native structure dramatically.

In the case of proteins, the denatured structure is often considered as or being identical to the unfolded state. The denatured structure as well as the unfolded state consist of amino acids linked together by peptide bonds with little long range interactions between the amino acids.

The rationale for the present methods for the folding of chain molecules, such as proteins and nucleic acids, in vivo as well as in vitro, can be understood by considering the backbone of the chain molecule in question as being an assembly of monomers.

Even for backbones which comprise a large number of non-coaxial chemical bonds of which many resemble free rotations, the presence of an environment such as water molecules, etc. prevents conformational changes from taking place in an arbitrarily small time. On a sufficiently short time scale, the position of the backbone will therefore be a stationary path. At correspondingly high frequencies, twiston and phonon excitations of the backbone will exist. Twistons are high frequency collective modes of the backbone involving twists around the path of the backbone.

In a simple instance, where the bonds of the backbone are coaxial and exhibit a free rotation, the symmetry becomes isotropic and collective twist modes do not exist (polyethylene, where the monomers are —$CH_2CH_2$— (or —$CH_2$—) is almost at this limit). If the free rotation around the bonds is constrained, or if some of the bonds are non-coaxial, a collective twist modes can be excited. This is the case of more sophisticated chain molecules, e.g. polypeptides/proteins and nucleic acids.

Due to delocalization of the electrons, the amide bonds in a polypeptide chain are normally fixed in one of two stable forms, namely the cis form or the trans form, of which the trans form is the energetically favoured form. Furthermore, each of the bonds defined by the torsional angles $\phi$ and $\psi$, again defined (as is common practice) by the atoms $C(C=O)_{i-1}$—$N_i$—$C\alpha_i$—$C(C=O)_i$ and $N_i$—$C\alpha_i$—$C(C=O)_i$—$N_{i+1}$, respectively, will normally fluctuate between the energy barriers depending primarily on the $C\alpha$ substituents and the corresponding torsional angle, but also on the $\phi$ and $\psi$ torsional angles of the preceding and succeeding amino acids. Because the backbone of a polypeptide chain consists of non-coaxial bonds, a change in the value of one of the dihedral (torsional) angles will also result in a curving of the polypeptide molecule leading to global changes of the path defined by the backbone. The presence of an environment to the polypeptide chain sets a lower limit for the time for such a change in the conformation of the backbone.

If radiation or vibration of a certain frequency is applied to the chain molecule in its environment either indirectly by an external source or directly by a molecular resonator system, resonance with a collective twiston of the backbone can be obtained. In this way, the amplitude of the twist mode of the backbone can be continuously increased until the backbone changes its conformation in order to drain the twist mode for energy. The resonating phenomena are signified by standing twist waves along the backbone. The patterns of standing twist waves define the details of the structural changes which are leading towards the final structure. It can be rationalized that the initiation point for the global transition will be a pre-defined location of the backbone which is determined by a combination of the symmetry of the twist mode and of local energy barriers. The locations are therefore not necessarily those with the lowest local energy barriers. Consequently, the structural transformation will proceed in a deterministic manner.

According to the invention, the change in the three-dimensional structure of a chain molecule having a one-dimensional primary structure comprising non-coaxial bonds is due to a catastrophic event initiated by excitation of a collective twist mode (twiston) of the backbone of said chain molecule. At relatively low amplitudes of the twist mode, the backbone can sustain the twist mode, but at a higher amplitude a catastrophic event takes place. This is the instability point where the amplitude of the twist mode is so large that it becomes unstable at the expense of formation of curvature in the backbone. As the backbone curves and moves through the medium, energy dissipation to the medium is enhanced.

Change in the three-dimensional structure of a chain molecule is sensitive to the following factors: the resonance frequency of the twist mode of the chain molecule, the frequency and the energy of the energy provided by a resonator, the relaxation of the twiston, and to energy dissipation; where the resonance frequency of the twiston is a given value which can be estimated from the constitution of the chain molecule or can be measured.

In a biological system, the length and thereby the eigenfrequency will be evolutionarily adjusted to the frequency of the resonator in the biological system, e.g. the molecular resonator system. In solution, the length of the peptide is pre-defined and if the frequency of the applied energy is far from the eigenfrequency of the chain molecule, the stimulation of the twist mode will not take place, and folding will consequently not be notable.

Thus, it is expected that the eigenfrequencies are almost universal for mammalian proteins such that roughly the same frequencies will initiate the twist mode. The indication for this is that large proteins (of more than 200 amino acids) consist of smaller domains having similar size with respect to the number of amino acids. Each of these domains has, hence, approximately the same eigenfrequency.

When sufficient activation of the twist mode is obtained, the backbone will bend in accordance with the topological considerations given in the Theoretical Section. At this stage, the backbone begins to continuously change its configuration, and it is possible that some substructures are formed. When the resonance phenomenon is dampened either by the removal of the stimulating source such as the microwaves, the molecular resonators etc., or by a change in the resonance frequency of the twiston due to a possible small shift in resonance frequency between the resonance frequency of the twiston of a (partly) folded and an unfolded structure, respectively. At this point the backbone can proceed to obtain its new structure.

Thus, it is within the scope of the present invention to change the functionality of three-dimensional structure representing a first folded state of the chain molecule to a three-dimensional structure representing a second folded state of the chain molecule. Similarly, the change from a folded state to an unfolded state, and vice versa, is also possible. In special cases, the desired structural changes are relatively minute, but large enough to introduce a relatively large change the functionality of chain molecule.

In one embodiment of the present invention the chain molecule is a protein or enzyme exhibiting a biological effect when present in the folded state.

One interesting example of this is the case where both the initial state and the final state are folded states, and where one or more species are trapped in a cavity, e.g., of the initial folded chain molecule; by excitation of a collective twist mode of the backbone of the chain molecule, the trapped specie(s) can escape from the cavity, whereby one or more functions of the chain molecule depending on the trapped specie(s) are altered. Similarly, the initial folded structure can be part of an aggregate which is disintegrated when a collective twist mode of one or more components of the aggregate are excited.

In an embodiment of the present invention the chain molecule, e.g. a protein, is aggregated with one or more component(s), which may be further chain molecules, when the chain molecule is in the initial folded state. Thus, by overcoming this problem, the aggregates are disintegrated by applying high frequency energy from an external energy source; a disulphide redox system is optionally added to the fluid system; and high frequency energy corresponding to the resonance frequency of the chain molecule is applied to the fluid system.

In the case of protein folding in vitro, formation of intramolecular, as well as intermolecular, —S—S— bonds in the correct positions can often be difficult. In refolding processes it is important that the reduction of one or more —S—S— bond(s) can take place in order to unfold a incorrectly folded structure and that the oxidization of two thiol groups to a cystine moiety can take place in order to lock a structure which has obtained the desired folding. Therefore, it is in most cases important that a disulphide redox system is present in the fluid system.

In the present specification and claims the term "disulphide redox system" is intended to mean redox systems which contain mixtures of reducing and oxidizing agents, the presence of which facilitate the breaking and making of disulphide bonds in a polypeptide or between polypeptides. Accordingly, "disulphide redox agents" are such reducing and oxidizing agents which facilitate the breaking and making of disulphide bonds in a polypeptide or between polypeptides. Thus, the disulphide redox system contained in a fluid system which comprises the proteins further comprises as a disulphide redox system a mixture of a mercaptan and its corresponding disulphide compound.

As an example, all cysteine residues in the polypeptide molecules may have been converted to reactive mixed disulphide products of either glutathione, thiocholine, mercaptoethanol or mercaptoacetic acid, during a unfolding (denaturing) or folding (renaturing) process. Such a converted polypeptide (fully disulphide-blocked polypeptide or protein) is a polypeptide or a protein in which cysteine residues have been converted to a mixed-disulphide in which each cysteine residue is disulphide-linked to a mercaptan, e.g. glutathione. The conversion of the cysteine residues to mixed disulphide products may be accomplished by reacting a fully denatured and fully reduced ensemble of polypeptide molecules with an excess of a reagent which is a high-energy mixed disulphide compound, such as an aliphatic-aromatic disulphide compound, e.g. 2-thiopyridyl glutathionyl disulphide, or by any other suitable method.

Examples of such mixed disulphides are glutathionyl-2-thiopyridyl disulphide, 2-thiocholyl-2-thiopyridyl disulphide, 2-mercaptoethanol-2-thiopyridyl disulphide and mercaptoacetate-2-thiopyridyl disulphide.

In interesting embodiments, the disulphide redox system contains glutathione, 2-mercaptoethanol or thiocholine, each of which in admixture with its corresponding symmetrical disulphide.

Thus, in the methods according to the present invention where the three-dimensional structure of polypeptides, proteins, or enzymes are changes and where these species comprise —S—S— bonds, is preferred that a disulphide redox system is present in the fluid system, or is added to the fluid system, in order to form or cleave any disulphide bonds which either will prohibit unfolding of a folded structure or will stabilize an obtained folded structure.

Another embodiment of the method is the use of excitation of collective twist modes in crystallization processes. The preparation of a protein crystal suitable for crystallographic studies is often time-consuming, and in some cases virtually impossible. This is probably due to the smaller or larger randomly occurring structural changes taking place in the solution. By applying high frequency energy following the guidelines given herein to a solution containing the protein, a solvent system, and optionally one or more additional components, either continuously or intermittently, while gradually removing the solvent system and optionally one or more of the additional components from the said solution, a solid containing the chain molecule may precipitate from the solution. Alternatively, the method may comprise gradually adding a solvent component or a further additional component to said solution, whereby a solid containing the chain molecule precipitates from said solution. In both cases the crystal structure may in addition to the chain molecule optionally have solvent molecules and/or additional component molecules incorporated into the crystal structure.

One reason for the difficulties of some proteins in forming large crystals is believed to be the formation of a coherent wring state of the proteins in the nucleation grain of the crystal. This can lead to amplitude so large that one of the proteins and therefore the crystal become unstable thereby hindering the growth of the crystal grain. A methods for overcoming this problem comprise of one or more of the following actions:

1. Use of damper molecules in order to reduce the wring mode activity. A damper molecule can be organic such as certain proteins, or inorganic such as e.g. carbon-60.

2. Use of a different solvent than water such that wring mode activity is damped when compared with the use of water. For small molecules it can in certain cases be possible to eliminate the need for a solvent. The crystals are then grown from a vapour.

3. When possible to select a temperature close to, but above, that for cold denaturation.

In the case where the chain molecule is a synthetic organic polymer, the properties of a material consisting of the chain molecule are dependent upon the three-dimensional structure of the individual chain molecules. In order to assist the folding towards preferred three-dimensional structures, certain collective twist modes of the backbone of the chain molecules may be excited, during the polymerisation process.

As described above, the application of high frequency energy to a collective twist mode can either be performed by using an external source or by using an internal source such as a molecular resonator system.

As external high frequency energy sources, a microwave source, e.g., a microwave generator connected to a microwave resonator is often employed. The term "microwave resonator" refers to an electromagnetic cavity with walls of one or more electrically conducting materials, meshes of such materials, or constructions made at least in part of electrically conducting materials. The electromagnetic cavity may preferably be used for microwaves with a wavelength which leads to a standing pattern in the cavity, but also for microwaves with other wavelengths. The microwaves are fed to the electromagnetic cavity from a microwave generator, such as a commercially available microwave generator, using a coaxial cable feeding an antenna or another electrically conducting structure inside the cavity. Alternatively, a microwave waveguide may be used to feed the microwave radiation to the electromagnetic cavity. In special cases the microwave generator and the microwave resonator appear as one unit, e.g. a klystron or magnetron in a microwave oven, or as a unit with solid state devices.

Another external means for obtaining the desired twist excitations is using a piezoelectrical crystal, such as a quartz crystal. The vibrating quartz crystal could be covered by a thin layer of the solvent comprising the chain molecule. The thickness of the layer is confined within a range of thicknesses that will allow for the quartz crystal to oscillate. The thickness of the solvent layer will normally be less than 10 $\mu$m, such as less than 1 $\mu$m. The quartz crystal can be submersed in the fluid system or be part of the wall of the reactor which contains the fluid system. In a special case several such quartz walls are used and the quartz crystals are operated in or out of phase. Furthermore, in the case when chain molecules are contained in a gas phase reactor one or more quartz crystals may also be used. In all the above cases involving quartz crystals, continuous flow or batch processes may be applied.

In some cases sufficient twist amplitude can be obtained by the use of either a continuous or an intermittent broad spectrum device. The device can be a circuit for the generation of electromagnetic radiation, or a device which generates broad-spectrum high frequency vibrations (reminiscence of white noise) such as for example a micromechanical device. These devices can be used in the same manner as discussed for the use of quartz crystals.

As an optimization feature, the application of high frequency energy may be performed intermittently, which will allow for the chain molecule to go into a "relaxation" state, or the application may be performed continuously. In cases where the amplitude is critical, the amplitude may be gradually decreased during the application of high frequency energy. When combined with the presence of a disulphide redox system, an extremely efficient folding/refolding processes is possible. The principles of refolding of enzymes outlined in WO 94/18227 (Denzyme) may, thus, be combined with the principles of the present invention.

As internal sources, molecular resonator systems may be applied. In the light of the understanding on which the invention is based, it seems natural to assume that Nature utilizes molecular resonator systems in biomolecular systems. Thus, in the case of protein synthesis and protein folding in vivo, it is natural to imagine molecular resonators present in the cell and being close to the protein or even attached to it. The molecular resonator can then directly transfer an oscillation with a characteristic frequency to the protein backbone, resulting in a twist mode. According to the invention, this insight is now utilized in a number of ways, e.g.:

1. By positively introducing or applying molecular resonator systems in environments/situations where they are not naturally present, and/or 2. By modifying existing molecular resonator systems to enhance their effect, or 3. By positively removing or modifying molecular resonator systems in environments/situations where they are naturally present, to counteract or avoid or reduce their effect.

When a molecular resonator system is introduced or applied to apply high frequency energy to a twiston, energy from an external source may be omitted; the molecular resonator system will be able to derive the necessary energy from inside the fluid system in question. However, energy, such as thermal energy may be applied from an external energy source, e.g. in order to adjust the temperature of the fluid system, and in some cases a molecular resonator system used with high frequency energy applied from an external source may exhibit a synergistic effect.

Thus, in an embodiment of the present invention the fluid system containing the chain molecule further comprises a molecular resonator system not native to the fluid system, said molecular resonator system comprising bonds having rotational and/or vibrational frequencies in the range of three times the full width at half maximum of the resonance of the chain molecule. When used in combination with an external high frequency energy source, the molecular resonator system is believed to be a system which enhances the effect of the externally applied high frequency energy.

Thus, one embodiment utilizing this principle is simply to add a molecular resonator system in the form of a chemical compound or chemical compounds to the fluid system.

Examples of chemical radicals or groups which are evident candidates as active resonator groups in molecular resonator systems are given in the following. Evidently, the chemical compound or compounds utilized for a particular task in a particular system must be selected on the basis of knowledge about the system and chemical compound(s) and the interaction between the system and the chemical compound(s), or empirically on the basis of suitable preliminary experiments, in all cases based on the understanding provided according to the present invention and utilizing the assessment methodologies provided herein. Not only the chemical identity, but also the concentration of the molecular resonator system, the time during which the system is influenced by the molecular resonator system (controlled, e.g., by having either the molecular resonator system or the chain molecule or chain molecules to be influenced thereby bound to a solid support and thereby separable from a fluid phase), the chemical environment influencing the chemical affinity between the molecular resonator system and the chain molecule or chain molecules, and the temperature are parameters which can be controlled to provide the desired resonator effect. This embodiment is contemplated to be most valuable in, e.g., laboratory or production scale folding or refolding processes.

One known example of the action of a molecular resonator system on a chain molecule is described in Baker et al., Proteins: Structure, Function, and Genetics 12, 339–344, 1992. Being known, this specific disclosure does, of course, not constitute part of the present invention. In the paper, however, the interaction between the chain molecule ($\alpha$-lytic protease) and the added chemical compound (the corresponding propeptide with which the $\alpha$-lytic protease is associated in the cell native to the $\alpha$-lytic protease) is proposed to cause a reduction of the free energy of the folding transition state, a proposition which does not disclose or indicate the principle of the present invention.

Thus, according to the present invention, the molecular resonator system is not native to the fluid system even if it consists of essentially the same components as the molecular resonator system of the native fluid system, because the concentration of one or more of the components of the molecular resonator system or the relative concentration between the components of the molecular resonator system is different than in the native system.

The present invention also relates to a method for changing the functionality of the three-dimensional structure of one or more chain molecules contained in a fluid system, each molecule having a one-dimensional primary structure comprising a backbone the predominant bonds of which are non-coaxial or rotational non-symmetrical, or of aggregates of such molecules, the method comprising applying energy to a twist mode of the chain molecules by means of a molecular resonator system not native to the fluid system and thereby initiate a structural change to result in a functionality of the three-dimensional structure which is different from the starting functionality of the three-dimensional structure.

With respect to the selection of molecules or types of molecules which are candidates for molecular resonator systems, it may be valuable to consider what must be believed to be the molecular resonator systems used by Nature. Thus, in many types of living cells, the molecular resonators which activate the twist-modes in the polypeptide chains are either part of a particular side-chain, part of a molecular complex built with one or several particular side-chains, or are part of another molecule in the cell which makes close contact to the polypeptide chain. The same principles can be applied in the selection or creation of molecular resonator systems for use in the present invention. Some very good candidates for molecular resonators groups at play in biological systems are the amino acids. For example, for the amino acids which contain one or more closed ring(s) of atoms such as proline and the aromatic acids phenylalanine (Phe), tyrosine (Tyr), histidine (His), and tryptophan (Trp), many of the vibrational, rotational and quantum mechanical modes couple directly to the backbone and can therefore couple to a twiston. Thus, it is presumed that effective molecular resonators of the peptide type comprises one, or preferably more, aromatic amino acid(s), in particular with a high aromatic substitution, such as, e.g., with a higher aromatic substitution than the naturally occurring amino acids. Interestingly, Phe and Tyr have similar excitations and are both present in enkephalines pointing to the possibility that enkephalines under certain condition may act as a molecular resonator, and indicating that analogous compounds with a higher aromatic substitution may be particularly effective aromatic resonators. Examples of candidates for synthetic non-peptide molecular resonator systems are morphine and related substances.

The molecular resonators make use of the fact that the vibrational and rotational states are thermally populated. The aim of the use of molecular resonators is to obtain a higher population of the twist mode of the polypeptide backbone than is present simply by its thermal population. The effect of the molecular resonator can further be enhanced by the use of two or more resonators simultaneously, as the coupling through the backbone of the polypeptide can force a coherent state. In this case the imposed amplitudes on the twist modes shall be added to each other, and the energy of the twist mode is therefore proportional to the squares of the numbers of resonators, rather than to the number of resonators which is the case for incoherent excitation of the twist mode. It may therefore in some cases be advantageous to use molecules having several resonator groups, or combinations, including aggregates or complexes, of several molecule species. In this way, a sufficiently strong amplitude of the twiston can be obtained. The strong dependence of the amplitude of the twist mode upon the number of molecular resonators makes this a controlling parameter for the protein synthesis. Length is an important criterion for resonance; but when resonance is first obtained, it is important for the protein synthesis that the cell has the option to reduce the amplitude of the twiston. It can be done by moving one (or more) of the molecular resonators away from the backbone. It can also be done by cutting the backbone to a new length. Interestingly, this option, in addition to changing the resonance frequency, may also remove molecular resonators if they are in the polypeptide chain that is being removed or if they are bound to one of amino-acids of the removed polypeptide chain.

Sometimes, the number of specific oscillators may be too low and the production of a given native protein structure is hindered. However, problems may also arise as a result of the numbers of oscillators being to large, as it may make it difficult for the biomolecular systems to control the process. The molecular resonators must have resonator groups which are very closely coupled with the backbone, thus, the first groups to think about as resonator group candidates are resonator groups corresponding to the molecular fragments associated with, or bonded to, the backbone of the chain molecule, e.g., the polypeptide chain. Such resonator groups include bonds or groups of bonds which may have a eigen mode of a frequency in the range where the collective twist mode of the chain molecule can be induced. In the biological system a chain fragment which may be presumed to contain a relevant number of resonator groups, e.g., a propeptide, is synthesized in connection with the synthesis of the chain molecule, e.g., the protein. In many cases, the propeptide is probably chemically connected with the protein during at least part of the folding of the protein in the biological system. However, it is often not always necessary that the propeptide is chemically connected with the protein at a stage during the folding, as the two peptide chains, i.e. the propeptide and the protein, can interact by other means.

While a direct resonator effect has been ascribed to propeptides as a main effect in the above discussion, it cannot be ruled out that a similar overall effect on the chain molecule could be due to an ability of the propeptide to ensure coherent coupling of resonators, and that such ability could supplement or be responsible for achieving the desired twist mode.

In accordance with these consideration, one interesting embodiment of the invention is the use of synthetic propeptides for the in vitro production of properly folded biologically active proteins, where the propeptides are simply added to fluid containing the protein to be influenced. The propeptide used in connection with a particular protein may be the propeptide used by Nature in the production of the protein in question, or one propeptide (or modified propeptide analog, e.g. with a higher concentration of aromatic substitution) may be used in connection with the folding of a range of proteins, provided that the necessary interaction exists in the system, which may be assessed by preliminary experiments or calculated accordance with the instructions given further below.

Special types of molecular resonators are those which function in particular is stimulated by an external source, such as a microwave source, but also by external sources of far infra-red, infra-red, visible, or ultra-violet light. An example of such a molecular resonator in Nature is the retinal molecule in Rhodopsin, which can absorb light quanta in the visible and ultra-violet range. Thus, the frequency of the electromagnetic radiation applied from an external source need not to be that of the collective twist mode of the chain molecule, by should be adapted to the molecular resonator system, which may have a broad window for activation by an external source.

Addition of a resonator system to a fluid system comprising the chain molecule(s) will in some cases enhance the effect of the applied microwave energy, simply by individually adding an effect to the effect of the applied microwave energy, or more interestingly by producing a synergistic effect in combination with the applied microwave energy. The methods described above wherein a resonator system is used which is not native to the fluid system and has a frequency equally to, or within the vicinity of, the resonance frequency of the chain molecule, are within the scope of the invention. By the term "vicinity of the resonance frequency" is meant a given interval around the frequency such as, e.g., three times the width of the resonance.

As described above, it is likely that biological systems take advantage of a certain molecular resonator system. Thus, it is likely that small peptides play an important role in the molecular resonator systems native to the cellular environment. In the case of proteins produced by recombinant DNA techniques it will therefore often be advantageous to incorporate coding for small peptides, which may act as molecular resonators (or otherwise facilitate a coherent resonance mode, confer above) and thereby facilitate folding of the desired protein, along with the coding for the desired protein. It is therefore within the scope of the invention to include one or more peptides in the molecular resonator system of the host cell in order to provide a molecular resonator system which is not native to the host cell, but which has components identical with or functionally equivalent to the components of the cellular system native to the protein. (In the present context, the term "functionally equivalent", as used about propeptides and analogues, indicates a similar functionality with respect to folding of the protein in question). Furthermore, in special cases it is advantageous to incorporate one or more peptide fragments in one or both ends of the protein. In this case the excitation of a collective twist mode can be performed when the protein is in the cell (in vivo) as well as after the protein is released from the cell (in vitro). In the latter case the peptide fragments must normally be cleaved from the desired protein after the folding of the protein.

In the case where the folding of a protein is performed in vitro by addition of a peptide identical to or functionally equivalent to the propeptide natively associated with the desired protein when the desired protein is produced in the cell by a natural process, it may prove necessary to induce the collective twist mode of the protein by means of an external high frequency energy source, such as a microwave source.

Thus, an embodiment of the method comprises:
selecting a molecular resonator system
(i) having a resonance frequency identical to or substantially identical to the eigenfrequency of the twiston of the chain molecule; and
(ii) having such an affinity to the chain molecule that it will allow for the molecular resonator system to couple with the chain molecule; and
introducing the selected molecular resonator system in the fluid system containing the chain molecule(s).

Furthermore, the resonance frequency of the chain molecule has preferably been determined prior to selection of the molecular resonator system.

In an embodiment the chain molecule is contained in a micro-organism, preferably the micro-organism is modified to produce a non-native molecular resonator system or a modified native molecular resonator system. Alternatively, the chain molecule, e.g. a protein, and the molecular resonation system are contained in the extracellular environment of a fermentation mixture optionally also containing the protein producing micro-organism or remains from the micro-organisms.

Often it can be of advantage to have the chain molecules anchored to a solid support. This greatly constrains the topological freedom of the backbone as the twist of the backbone is hindered at the substrate and thus defines the types of twiston which can be effective. A further option is to anchor the backbone in both ends when possible.

Thus, in an embodiment the fluid system further comprises one or more solid phase support particle(s), and the chain molecule is attached to the solid phase support at least during the application of high frequency energy. In particular, the high frequency energy is applied to the fluid system in order to change the functionality of the chain molecule from the functionality of an unfolded form to the functionality of a folded form.

Thus, in the case of synthesizing proteins on a solid support, the solid support material can be selected from the materials known per se. Problems caused by aggregation or partial folding of the protein or polypeptide fragments can be solved by applying high frequency energy to the twist mode of the protein or polypeptide anchored to the solid support continuously or intermittently during the synthesis or after the completion of he synthesis. It is in some cases interesting to treat a fluid system comprising the polypeptide attached to the solid support in order to retain the proteins in an extended, i.e. an unfolded, form whereby the terminal and/or the side-chains of said chain molecule are accessible for chemical reagents. In this way the coupling of amino acid monomers can proceed. Another interesting example of the applicability of the method is the case where application of high frequency energy leads to a folding of the synthesized protein or polypeptide. In this case the formation of intramolecular —S—S— bonds can be performed while the protein chains are still attached to the solid support, and unwanted misfolding and formation of intermolecular —S—S— bonds can thereby be minimized. Thus, a disulphide redox system is preferably present in or added to the fluid system comprising the immobilized polypeptide or protein if —S—S— bonds are required in order to stabilized the desired three-dimensional structure.

Many interesting polypeptides and small proteins have difficulties in being folded or refolded in vitro. This is probably due to the fact that the frequency of the twiston of such a short backbone is higher than the frequency of a longer backbone, and that, therefore, resonance conditions therefore are not obtained due to the lack of resonators which can supply energy having a frequency in the relevant frequency range.

Thus, in an embodiment the chain molecule is a polypeptide and a collective twist mode of the backbone of said polypeptide is excited by high frequency energy, said polypeptide being too short to be excited by intracellular sources in biological systems.

In biological systems these polypeptides and small proteins are produced with no obvious problems. Also, it seems as most of the domains of folded proteins are of roughly the same size, about 70–130 amino acids. This fact seen in the light of the teaching of the present invention suggests that protein folding in biological systems is performed domain-wise. In this way the biological system can take advantage of a narrow frequency band likely present in the biological system. In the case of insulin, a precursor is synthesized as one chain of about 110 amino acids and that the final cleavage takes place after the folding, whereby insulin having an A-chain and a B-chain of 21 and 30 amino acids, respectively, is obtained. Thus, in the insulin case it is assumed that the long intermediate chain length of the protein is essential for folding and for formation of the —S—S— bridges.

Thus, the present invention provides a method for the preparation of a desired polypeptide having a desired three-dimensional structure, the method comprising:

preparing a fluid system comprising a polypeptide comprising a sequence part identical to the sequence of the desired polypeptide, said polypeptide further comprising a sequence part or sequence parts which will ensure that the entire polypeptide has a collective twist mode which when stimulated will result in said desired three-dimensional structure of said sequence part identical to the sequence of the desired polypeptide;

exciting said collective twist mode under conditions with respect to source and parameters involving frequency, amplitude and duration which will initiate a structural change to result in the desired three-dimensional structure of the desired polypeptide, provided that substantially no decomposition of the backbone of the desired polypeptide is caused when said excitation is performed by application of high frequency energy;

optionally forming one or more —S—S—bonds by using a disulphide redox agent.

cleaving the bond(s) of the polypeptide upstream and/or downstream of the desired polypeptide with substantially no alteration of the three-dimensional structure of the desired polypeptide.

One evident fluid system for this purpose is a microorganism which harbours recombinant DNA encoding the (fused) polypeptide. Cleavage of the fused polypeptide with the desired three-dimensional structure of the sequence corresponding to the desired polypeptide may, e.g., be performed by using enzymes, such as proteases, or by selective hydrolysis of the target bond(s).

The term "micro-organism" is used in its normal meaning and indicates organisms such as viruses, bacteria, fungi, yeasts, etc.

Another way of solving the problem of folding or refolding of polypeptides or small proteins arising from cleavage of larger proteins is to apply energy at a frequency corresponding to the frequency of the twiston of the smaller molecule. In this case the required frequency of the energy will be slightly higher than the frequency required when folding longer proteins, and as the folding follows a deterministic pathway, the resulting three-dimensional structure may not always be identical to the three-dimensional structure of the sequence incorporated in the folded larger protein.

An example of an important problem encountered in the biotechnological industry when producing proteins from recombinant DNA, i.e. proteins not native to the host cell, is the formation of inclusion bodies. This problem occurs because the expressed protein is non-native to the host micro-organism, e.g. a bacterial species, whereby the micro-organism pacifies the foreign product, e.g., by forming inclusion bodies, which are expelled from the cell. By use of the present invention, e.g. by applying microwave energy to the micro-organism culture in accordance with the principles described herein or by incorporating a suitable molecular resonator system in the micro-organism, this problem can be solved.

Thus, e.g., the fermentation vessel system (which may be a fermentation reactor adapted to batchwise fermentation or a continuous type fermentation vessel system) may be equipped with means for supplying microwave radiation in the appropriate wavelength range, either to the total contents of the fermentation vessel system, or to one or more domains in the vessel specially adapted thereto, suitably equipped with reflectors or agitators in a manner known per se. When the fermentation vessel system is to comprise electrically conductive walls or domains comprising electrically conductive walls or grids, the walls or grids can utilized as electromagnetic cavities or as wave guides. The electromagnetic energy can be generated by means of a microwave generator arranged in or adjacent to the reaction vessel system and be connected to the cavity in question by means of wave guides or coaxial cables.

The conditions to be applied with respect to parameters involving wavelength, amplitude, treatment time and frequency relative to the development of the culture will be adapted to the individual protein to be produced and the folding behaviour of the protein in the micro-organism, so as to ensure that the proper folding into the desired functional protein will preferably take place before formation of inclusion bodies. These conditions are suitably established by preliminary experiments. Assessment of the stage of development of the culture may be based on predetermined (preprogrammed) setups with respect to the time, chemical environment and/or physical environment, or on chemical or physical measurement performed on withdrawn samples or in situ on the culture.

In vitro, and in some cases also in vivo, the disintegration of aggregates of chain molecules, such as inclusion bodies, can be performed simply by applying high frequency energy to the fluid system containing the chain molecules, e.g., by using one of the setups described herein. In the case of refolding or folding of proteins comprised in inclusion bodies in vitro, the inclusion body is preferably disintegrated prior to the application of high frequency energy, e.g. by addition of a denaturing agent.

The expression "denaturing agent" refers to a compound which when present as in a fluid system comprising the chain molecule, e.g. a polypeptide or a protein, may destabilize the folded states of the chain molecule leading to partial or complete unfolding of the chain molecule, e.g. the protein. The denaturing effect exerted by a denaturing agent increases with increasing concentration of the denaturing agent in the solution, but may furthermore be enhanced or moderated due to the presence of other solutes in the solution, or by changes in physical or chemical parameters, e.g. temperature, pressure, and pH.

As examples of suitable denaturing agent to be used in the method according to the invention may be mentioned urea, guanidine-HCl, di-$C_{1-6}$-alkylformamides such as dimethylformamide and di-$C_{1-6}$-alkylsulphones.

It is in most cases advantageous to gradually remove or pacify any denaturing agents present in the fluid system while the excitation of a collective twist mode of the backbone of the protein is performed in order to allow formation of intramolecular bonds.

Thus, in order to avoid aggregation of the polypeptides chains while a collective twist mode of the backbone of the protein is excited, a denaturing agent, such as urea, is first added until sufficient denaturing is obtained. Then microwave radiation of a frequency corresponding to the resonance frequency of the chain molecule is applied to the solution while the denaturing agent is gradually removed (or pacified). In this way the application of high frequency energy ensures that the polypeptides or protein chains obtain the desired folded structure and at the same time prevents aggregation of the chain molecules into inactive clusters of molecules.

An important scenario in which a change of the three-dimensional structure of one or more chain molecule(s) by excitation of the twist mode of the backbone of said chain molecule(s) is performed in order to avoid aggregation of the chain molecule(s), is the in vivo scenario in which a culture of microorganisms producing the chain molecule(s) is subjected to microwave radiation either intermittently or continuously.

The method according to the invention can be used to suppress the tendency to aggregation of proteins, and in some cases to reverse an unwanted process. As a valuable example of use, an animal, such as a human, can subjected to high frequency energy from an internal source, such as a molecular resonator system, or from an external source, such as a microwave source in a selected narrow band, to prevent adverse aggregation or proteins, and/or to reverse adverse processes involving proteins in particular three-dimensional structures. The application of the high frequency energy can be localized or focused to a particular site or tissue. It is obvious that only a narrow frequency range around the frequency at which the desired modification takes place should be used in order to avoid adverse side effect such as, e.g. heating of tissue. This is the case when the frequency width does not exceed the width of the twiston. Keeping a narrow frequency width and using focusing setups tend to limit undesired side-effects. It is contemplated that this new therapeutic method may achieve considerable importance in the treatment of adverse conditions involving particular three-dimensional configurations of particular proteins, or changes in the configurations. A few examples will be given: In Alzheimer's disease, an undesired aggregation of polypeptide chains takes place after a conformational change has taken place. Using the therapy method of the invention, the conformational change and the aggregation are counteracted by application of microwaves of a frequency which will activate a twiston at an amplitude large enough to temporarily change the three-dimensional conformation and thereby initiate a reversal of the adverse structural change which has taken place. Another example is the "shaking off" of sugar moieties from decayed glycoproteins, that is, glycoproteins on which additional carbohydrates have become attached, thereby making it difficult for the immune system to recognize the glycoproteins, a strategy used by cancer cells. The excitation of twiston modes of the folded protein, e.g., by means of microwave energy, corresponds to a shaking of the protein. A shaking of the protein by the twiston can shake off such undesired hydrocarbons. An example in which "shaking off" of undesired carbohydrate groups by application of microwave energy is in therapeutic treatment of cataract and similar vision disorder. The hydrocarbon caused crosslink of the proteins in the lens of the eye can be prevented and in some cases reversed.

In an embodiment of this application of the invention consists of prophylactic treatment of patients which are in special risk groups for the development of reduced sight. First one must determine the frequency where a favoured interaction with the lens material can lead to the desired effect. A desired effect can be obtained at the resonance frequency for the involved proteins, or at a harmonic (below the 10th) hereof. In certain cases the effect can be maximized be using a frequency off the resonance. A special apparatus is constructed for use in the treatment of the patient. In one construction a quartz crystal is utilized to vibrate a specific area of the lens. The vibrations are transmitted by the use of a very thin layer of fluid placed between the lens and the apparatus. The apparatus is moved around to especially bad places on the lens. Another construction of an apparatus is based on the use of electromagnetic radiation. A special generator of microwaves is constructed such that the treatment can be provided by the use of a headset. The treatment is repeated at regular intervals.

It is possible to take advantage of molecular resonators in order to achieve a desired functional change. For example, antibodies with incorporated molecular resonators, e.g., of the types described above, can thereby combine a passive function with an active function on the antigen molecule. The passive function is a binding (such as docking) due to geometrical and/or chemical affinity, while the active function involves an application of molecular resonators which can lead to changes in the antigen molecule. Even small changes in the antigen molecule can block its biomolecular function. In this way the blockages are obtained by a combination of geometrical blockages and reduction of the activity of the antigen molecule. Antibodies with incorporated chemical principles functioning as resonators may be prepared by chemical modification of antibodies or functional antibody fragments, or by recombinant DNA techniques. It may also be important to confer "anti-resonator" effect to antibodies to damp undesired or adverse resonances of antigens.

These principles can be extended to the use of further molecules in addition to the antibodies. The purpose of these molecules which dock to the antigen-antibody complex at a site different from the epitope in question, is to change the amplitude of the twist mode in the antigen and/or antibody and thereby enhance the desired antigen-antibody interaction. Thus, in this way, several molecular resonators or dampers may simultaneously influence and change the twist mode of the chain molecule while geometrical blocking also takes place by the antibody.

Thus, molecular resonators or dampers can play a crucial role in designing and modifying biomolecules. One of the basic interactions, e.g. between ligand and protein, can be understood as a twist mode that is initiated by transferring a resonance frequency between the molecular resonator and the biomolecule to be modified. (Other aspects of the interaction are, typically, H-bond formation, etc.). This results in a desired functional change. Candidates for such molecular resonators can be small neuropeptides, steroids, lipids, peptides or simply amino acids such as, e.g., glutamate neurotransmitter. In a case where twist modes play an important role in causing conformational changes in the protein ligand complex, one identifies the ligand as the molecular resonator operating on the protein.

Also in these cases, the change of the three-dimensional structure of one or more chain molecule(s) by excitation of the twist mode of the backbone of said chain molecule(s) may be performed in order to "shake off" unwanted moieties, the moieties being bonded covalently, ionically and/or by van der Waal forces to the backbone and/or to any side chain(s) attached to the backbone. It will be understood that the efficiency and concentration (and number of possible different species) of the molecular resonators must be adapted to the task to be performed, and that breaking covalent bonds will, of course, require coherent action of several resonators.

By application of the high frequency energy, e.g., in form of microwave energy or by introduction of a molecular resonator system, it is advantageous to predetermine the resonance frequency of the collective twist mode of the chain molecule in order to obtain a large effect from a low dose of high frequency energy, which then is applied in a relatively narrow frequency range, or from a low concentration of a molecular resonator, which comprised resonator groups having eigen modes allowing for the high frequency transfer to take place. Examples of methods for the determination of the resonance frequency of a chain molecule or an aggregate of chain molecules are described below.

The resonance frequency of a chain molecule can be estimated by using formula I in the Theoretical Section. However, in most cases it is desirable to have a more precise assessment of the resonance frequency, especially in cases where a narrow band of high frequency is preferred. In the following, two examples of measurement of the resonance frequency are given.

The invention also provides a method for determining the resonance frequency of a collective twist mode of chain molecules, or of aggregates of such molecules, where a microwave spectrum is obtained for the molecule in question, e.g. by using a conventional apparatus for measuring microwave spectra, and where an absorption frequency in the range 0.1 to 100 GHz, such as in the range of 0.2 to 10 GHz e.g. the range of 0.2 to 0.6 GHz, or 0.6 to 1.0 GHz, or 1 to 10 GHz, is then identified.

The present invention further provides a method for determining the resonance frequency of a collective twist mode of chain molecules, or of aggregates of such molecules, where a frequency range of the high frequency energy, e.g. from 0.1 to 100 GHz such as from 0.2 to 10 GHz or from 0.5 to 5 GHz, is scanned with a step size in the range of 0.25 to 250 MHz such as in the range 1.25 to 12.5 MHz, under simultaneous monitoring of the change of three-dimensional structure of said chain molecule, e.g. measuring the biological effect of the chain molecule or by using the viscosity/friction apparatus setup described herein, the resonance frequency being identified as the frequency at which the maximum change in the monitored condition takes place.

New materials produced by stimulation of twistons of the backbone of chain molecules As it appears from the above discussion the stimulation of collective twist modes of chain molecules leads to a predetermined folding of the chain molecule. When a ensemble of chain molecules in a concentrated solution is treated with high frequency energy, the similar folding of the individual chain molecules can in some cases result in a packing of the chain molecules in compact and well-defined structures such as fibers, sheets, bodies or other macro-structures. This is similar to the packing of proteins in a naturally synthesized fibers, such as silk fibers. Thus, a very structured and compact, and therefore highly desirable, packing of an ensemble of chain molecules can be obtained. The method applies especially to proteins, including tailored proteins, and to synthetic organic polymers.

Thus, the present invention also relates to the use of an aggregate of chain molecules in textiles, fibers, sheets, bodies, etc., said aggregate of chain molecules being constructed by applying energy from a high frequency source to an ensemble of chain molecules, preferably identical or substantially identical chain molecules, each having a one-dimensional primary structure comprising a backbone the predominant bonds of which are non-coaxial or rotational non-symmetrical, in order to change the functionality of at least a part of the chain molecules.

The chain molecule are preferably contained in a concentrated solution, and high frequency energy is applied from an external source, such as a microwave source. In a relevant setup, the microwave energy is applied, either continuously or intermittently, while the solvent of the solution containing the chain molecule is gradually removed, whereby the concentration of the chain molecule will exceed the concentration where the chain molecule will precipitate from the solution. By applying high frequency energy, the each chain molecules will have a well-defined three-dimensional structure, and in the case of identical, or substantially identical, chain molecules, the chain molecules will precipitate as well-ordered structures. The solubility of the chain molecules can also be lowered by reducing the temperature, whereby the same effect as by removal of the solvent can be obtained.

In a particularly interesting embodiment, the aggregate of chain molecules further comprises other species, e.g. micro-organism(s), enzymes, etc., whereby a macro-structure showing a biological effect is obtained.

Also, it can be envisaged that when aggregates of chain molecules are forming a membrane, induction of a change in the three-dimensional structure of the chain molecules by excitation of the collective twist mode of at least a part of the chain molecules, will lead to a change in the permeability of the membrane for a group of molecules. For a specific type of molecule the alteration, e.g. increase or decrease, of the permeability is highly desired in filtration processes. In order to stimulate the individual chain molecules, the membrane is preferably arranged in a electromagnetic cavity. By applying the pulsating high frequency energy, in may be possible to increase the permeability for a selected group of molecules.

Examples of systems where molecular resonators alter the function of a given set of target proteins As described above, there are basically two types of molecular resonators: (i) the ones that are thermally or chemically stimulated and (ii) the ones that are sensitive to external stimuli (such as light). In the following are described examples of how these types of molecular resonators can be employed to the solution of problem in the medical and biological sciences.

Immunology

For a given antigen its surface is exposed to attack from antibodies. The precise interaction and the affinity of the binding is dependent on detailed geometry of the surface conformations and can be described as a handshake. As described above, molecular resonators can be steered to make a specific change of the surface conformation and, thus, change the nature of the hand-shake. In such a picture the hand-shake can either be loosened up (lower affinity) or be tightened up (higher affinity) by an alternation of the local curvature in a certain area on the surface of the protein, or by a different surface alteration. A decrease of the antigen-antibody affinity is desired in the case of an auto-immune disease where one of the proteins of the host undesirably is being attacked by antibodies. In such a case it is desirable to change the twist mode, or amplitude thereof, in the protein with the antigen as the twist mode has influence on the antigen-antibody affinity. In accordance with this invention the twist mode of the protein with the antigen can be changed by an alternation of the amino acids sequence to either accommodate more molecular resonators or fewer than in the original sequence of the protein. The necessary changes in the amino acids sequence may be obtained by the use of gene therapy. Alternatively, the change in the twist mode can be obtained by one or more peptide chains, or other molecules, which are constructed, or chosen such that they can make a docking to the protein. The peptide chains, or molecules are chosen such that the number of resonators applied to the protein in question is changed. One examples of an auto-immune diseases is multiple sclerosis. The patient is submitted to treatment by exposure to electromagnetic radiation, intermittently and in some case continuously. The electromagnetic dose is applied to the brain and neural tissue of the attack. In certain cases the patient will have to carry a properly placed transmitter.

HIV

The case of virus proteins is well illustrated by the following HIV-protein scenario. At a crucial time in the beginning of the infection, the virus can bind to T-cell receptors, CD4 via its envelope protein GP120. After such an interaction a conformation is triggered so the protein is released and uncovers beneath it the membrane bound protein GP 41 that has a "spear" sticking out at about 50 degree relative to the surface. When inserted in the host T-cell plasma membrane the GP 41 protein initiates the fusion of the HIV virus with the T-cell. If the angle of the spear is altered by the application of a molecular resonator it is possible to stop the cellular fusion. The small peptide, Melittine, is known to have some effect on the GP 41 surface conformations and specifically on the angle of the spear, although the effect is not large enough to be effective as a treatment. In accordance with the teachings of the present invention, one of the actions of the Melittine peptide is to change the twist mode, or amplitude of, in the GP41 protein. This action can be enhanced by modifying the amino acid sequence to include more molecular resonators, e.g. by adding amino acids with more aromatic side-chains, and/or to incorporate Melittine into a larger peptide chain with a different twist mode activity. The treatment of the patient is done by administrating this medication to the patient, in some cases intervenously.

Photoactivatable resonator principles

The light harvesting protein complexes, such as Rhodopsin, contain a ligand (the chromophore retinal) that is responsible for the absorption of a photon and resulting in a proton transfer through the Schiff base. The ligand can be considered as a molecular resonator which is sensitive to light stimuli. Such light harvesting protein complexes can be designed so that they can be used as or like light-activatable resonators that can change a twist mode. One of the actions of a light sensitive molecular resonator is an intermittent activation of a twiston. Resonators can be produced for medical use with a light triggering mechanism. In special cases it can be advantageous to replace the triggering mechanism to being dependent on electromagnetic quanta of a different wavelength which can better be administrated to cells inside the human body.

Narcotics

One type of molecular resonators are molecules that bind to certain receptors with the purpose of causing (small) conformational changes leading to a desired change in functionality. One such example is the design of drugs with respect to a resonating effect, e.g., optimising positions of potential resonating side chains or chemical bonding. By such a tailor-made change in the native structure of a protein a change in the functionality is obtained.

An illustrative example of that is the opiate receptor binding to small peptides. Enkephalines, Dynorphines, etc. When the peptide binds to the opiate receptor, nerve signals are not transmitted, either due to blocking of an ion channel or due to a change in the functional linking to another effector system, such as through G-binding proteins. Such a change in the structure is likely to be induced by a change in twist mode, or amplitude. Mutation experiment have shown that a phenolic aromatic side chain (Tyr) is necessary at the N-terminal for getting an effect. The more potent morphine molecule has one aromatic ring, but is more rigidly arranged. The even more potent agent PET, 7-(1-phenyl-3-hydroxybutyl-3-)endoethenotetrahydrothebaine has two aromatic rings. In future design of narcotics considerations concerning which frequency modes these molecules can couple to are important, and it is contemplated that the incorporation of additional aromatic substitution in these molecules, beyond their present aromatic content, will lead to even more potent narcotics for use in critical pain-relieving applications.

As described in the theoretical section standing wring modes are responsible for structure formation of proteins. The wring modes are also responsible for the function of the native protein as a change in the standing wring pattern can lead to the ability of a protein to function in a certain respect or not. And not the least important, in some cases standing wring modes are responsible for biological communication. Desired changes in standing wring modes in desired proteins can therefore lead to a desired signal transfer and hence to therapeutical results. One method composed of exposing the patient to microwave radiation, intermittent or constant, locally by a special transmitter, mounted as bandage, inoperated into the body, or an external device which can be handhold, clamped to the body, or a stationary device filling an entire space or room with microwaves/radiowaves. The power of the microwave dose is adjusted such that the desired action is obtained and such that the power absorbed by the patient is of no or relative minor discomfort to the patient.

It is envisaged that high frequency energy may be used in the treatment of a number of diseases such as diabetes, haemophilia diseases (haemophilia A/B, Christmas disease), cystic fibrosis, sickle cell anaemia, diseases of infection such as viral infection, e.g. influenza, HIV, ebola virus disease, hepatitis such as hepatitis A, hepatitis B, hepatitis non-A, hepatitis non-B, and hepatitis δ, and polio; parasitic diseases such as malaria and river blindness; bacterial infections such as staphylococcus related diseases, salmonella infection and borrelia infection; diseases connected to auto-immunity such as multiple sclerosis and rheumatism; prion related diseases (such as the class of transmissible spongiform encephalopathies (such as Creutzfeldt Jakob disease)); diseases not connected to or yet identified as being prion caused such as Alzheimer's disease and health concerns of relatively unknown origins such as certain heart and cancer diseases, as well as aging, where similar effects of dynamical induced structural changes in proteins and DNA are present and can therefore be controlled by means of the techniques describe herein.

As is apparent from the above, a number of conditions and diseases in the mammalian body, e.g. the human body, are caused by undesired functions or states of proteins. For the sake of simplicity theses conditions and diseases may be categorized in three main groups: (a) conditions and diseases related to aggregation of proteins; (b) conditions or diseases related to the presence of an abnormal protein product; and (c) conditions and diseases related to the function of undesired proteins.

As has been discussed in detail above, the present invention and the underlying theory provides guidance for giving relief for these types of protein related conditions and diseases by applying high frequency energy under conditions with respect to frequency, amplitude, and duration which result in a change in the three-dimensional structure of the protein(s) involved.

Thus, the present invention also relates to the use of a high frequency energy source for the preparation of a device for the treatment of conditions or diseases in the mammalian body caused by the aggregation of proteins. Examples of such diseases and conditions are Alzheimer's disease, prion-related diseases such as the class of transmissible spongiform encephalopathies, e.g. Creutzfeldt-Jakob disease, etc..

The present invention also relates to the use of a high frequency energy source for the preparation of a device for the treatment of conditions or diseases in the mammalian body caused by an abnormal protein product. Examples of such diseases and conditions are Haemophilia A, Haemophilia B, Christmas disease, cystic fibrosis, sickle cell anaemia, and cancer.

Furthermore, the present invention relates to the use of a high frequency energy source for the preparation of a device for unfolding proteins causing conditions or diseases in the mammalian body, in particular where the conditions or diseases are associated with undesired attachment of cells or vira in the mammalian body. Examples of these diseases and conditions are influenza; HIV; ebola virus diseases; hepatitis vira diseases; infection from bacteria such as staphylococcus, salmonella, and borrelia; multiple sclerosis, and cancer.

In particular, the frequency range of the energy source used for the preparation of a device for the treatment of various diseases is adjusted to the eigenfrequency of the protein or resonator molecule involved in the disease in question, either by estimating the eigenfrequency or by determining the eigenfrequency in an in vitro experiment. In the case of unfolding of protein, the device preferably applies a frequency off resonance.

For the uses describe above the device may be any of the high frequency generators describe herein, e.g. microwave resonators, vibrating crystals, e.g. piezoelectric crystals, such as quartz crystal, a circuit which generates broad-spectrum high frequency radiation, or a device which generates broad-spectrum high frequency vibrations (reminiscence of white noise). The device for the various medical uses claimed herein, may either be adapted for insertion/inoperation into the mammalian body or may be adapted for external application of high frequency energy, such as a handhold device, a device mounted in a bandage, a device clamped directly to the body, or a stationary device filling an entire space or room with high frequency energy.

One of the more elegant ways of introducing high frequency energy may be to use a solid state emitter or a piezoelectrical crystal, such as a quartz crystal incorporated into the relevant part of the body of a human being, e.g. a tumor or the brain of an Alzheimer's patient.

As describe above, the device may apply the high frequency energy intermittently or continuously. The amplitude of the high frequency energy may be gradually or incrementally decreased, gradually or incrementally increased, or varied harmonically, in order to optimize the dose/effect ratio.

Because the only minor side effects may be tolerated it should be considered to used a device for the uses described above having a relatively narrow frequency band width. Although the band width may be considered in for the individual applications (diseases and conditions), the band width of the applied high frequency energy at half maximum should preferably be at the most 0.1 GHz, such as at the most 10 MHz, e.g. at the most 100 kHz, and for particular application it may be advantageous and maybe even required to us high frequency energy having a band width at half maximum is at the most 1 kHz.

A special case of therapeutical use is when the desired action is obtained by a combination of electromagnetic radiation and of administration of drugs. In this case the effect of the drug is enhanced, e.g. by a synergistic effect, in some cases it is also activated, by the electromagnetic radiation.

Thus, the present invention also relates to the use of a high frequency energy source for the preparation of a device for the stimulation of a drug-receptor interaction in the mammalian body.

A further special case of therapeutical use is when the action of the electromagnetic radiation is specifically target at preventing aggregating and in some cases dissolving aggregates of chain molecules within the human body. Notable, to prevent the advancement of diseases such at Alzheimer's, pion-originated diseases, unwanted blood and lipid corrugating, but in some cases also for preventing bleeding when one of the molecular agent (factor) in the body for stimulating blood corrugation is failing, or when corrugation need to be stimulated just needs to be stimulated.

Electromagnetic radiation can be applied with success as can be demonstrated by the following experiment. One can compare the-outflow of blood from a piece of beef broiled in a conventional oven, where the temperature in the center of the beef does not exceed, e.g., 55° C., and in a microwave oven, where the same temperature also is below, e.g., 55° C. The outflow of blood will be significantly different illustrating the microwaves influence over the blood coagulation and the flow of blood in connection with broiling of beef (and where the temperature apparently has no influence on the coagulation). The experiment is repeated a number of times with and without application of electromagnetic radiation with a reasonable chosen frequency. From the statistic one can demonstrate the advantageous of electromagnetic radiation.

From the description of the phase diagram it can be learned that the route to the folded structure can be taken either from the cold-denaturated state or from the hot-denaturated state, some times with success and some times without success as the cases will have different wring amplitudes. It is also learned from the phase-diagram that the folded protein have a standing wring pattern, and that for some proteins this wring activity is important for their stability. One embodiment of this invention is therefore to fixate a hot-denaturated protein for example in a gel, changing the temperature, pH, concentration of denaturation agent, such that the protein is transformed into a cold-denaturated state while folding attempts has been prevented. Now, the fixation is released, and the solvent is again changed such that folding can appear. By repeated this methods a few times a high yield of correctly folded proteins can be obtained.

Theoretical Section

An analysis of the geometrical nature of the protein backbone results in a winding topology for the peptide chain. The winding state defines a long range order along the backbone of a protein giving rise to long-range excitations (twistons). According to the invention the folding of proteins may occur when the amplitude of a twist excitation becomes so large that it is more energetically favourable to bend the backbone. The initiation of protein folding is a resonance phenomenon, and the subsequent conformational changes are highly guided and restricted by topology. While this theory has primarily been developed for proteins, it is evident that it can be extended to other chain molecules, as for example poly-nucleic acids and organic polymers.

The length of the polypeptide chain of globular proteins is much longer than typical diameters of the molecules. Yet, with the possible exception of some very short proteins, the polypeptide chain never displays a knotted topology. Thus, the disparity between different protein folds cannot be due to differences in their knot topology.

According to the present invention, protein folding is viewed not primarily as a phase transition driven by entropy, but rather as a transition leading to a catastrophic event. Only folded structures which are stabilized by hydrogen bonds, disulphide bridges, etc. can maintain a significant fraction of proteins folded. Although, the proposed mechanism for initiation of folding of polypeptide chains is general, the biological evolution of living organisms selects proteins with the ability to acquire stable conformations.

There have been earlier attempts in molecular biology to apply topological methods in structural analysis of macromolecules. Most studies have investigated supercoiled DNA, and differential geometrical aspects of biological membranes. For circular DNA it was possible to utilize the concepts of twist, writhing and linking to establish a conservation law, and for membranes to obtain a comprehensive differential geometrical analysis of phase, vesicle formation, and critical exponents. Further, topological methods have been applied to protein structures for the purpose of energy minimization. Topological constraints can lead to a deterministic model of folding. In contrast to earlier views, topological folding may not necessarily lead to a folding path that minimize the sum of self-interactions. Rather, the physical reason for folding to follow topological constraints is the interaction of a protein with its environment.

Winding

Next the winding of the protein backbone is investigated. By winding is meant the ubiquitous phenomena which may be observed in everyday life when dealing with items such as telephone cords, water hoses in gardens, pump hoses at self service gas stations, etc. Basically, unless these tubes are handled with great care, their unwinding requires large motions in the space of the tube. As the protein folds in interaction with its environment (e.g. in vivo), such large motions of the protein backbone are unlikely. It would be a lot easier to wind the water-hose on the reel in the garden if there was no gravity and the water-hose could avoid interaction with the ground. This is not physical, likewise for protein folding the interaction with its environment plays a crucial role.

The winding of the tube is defined as the number of rotations the end of the tube has made relative to the other end. This number is determined by the path of the tube, but cannot be calculated as a continuous measure depending uniquely on the local geometrical progression of the path. The reason for this is that the path is not closed or extended to infinity. In order to assign winding to a polypeptide backbone it is necessary to know what path the backbone has taken during folding. However, this folding pathway is most often unknown. Instead one can work with protein backbones that are extended to form a closed curve (or are extended to infinity). The winding of the backbone can thereafter be found as the linking of the curve which is topological conserved.

Most biological chain molecules, as for example proteins, are not circular but in principle linear, though they may be folded and densely packed into complex structures. A linear chain molecule in vacuum cannot sustain the above mentioned wring modes of circular chain molecules. The reason for this is simple; the linear chain molecule is strictly speaking not topologically constrained. However, in the physical and biological systems considered in this paper, there is viscous and/or disperative interactions which are caused by the interaction of a linear chain molecule with its environment. For proteins, the interaction take place with the aqueous environment, with other proteins, with membranes, etc. Due to dispersion, the topological restriction described by the White theorem is reintroduced, when a sufficiently short time scale is considered. The interaction with the environment is limiting the speed at which changes in structural conformations can take place. If the time required for a structural change becomes longer than the cycle time for the wring mode, the linear chain molecule can be said to be effectively topologically constrained. The time it takes for one part of a polypeptide chain to move through distances that are comparable to the separation distance to the other parts of the chain is known from fluorescence energy transfer measurement to be about $10^{-6}$ s. This range sets the limit for which time scales topological phenomena are valid for denatured polypeptide chains. The width of the eigenfrequency resonance for a wring mode is determined this consideration and the amount of dispersion.

Twistons

Associated with a particular path of the backbone is a geometrical orientation. One can define a ribbon, or a frame, by assigning a vector-field for this purpose. Nevertheless, even in the absence of a ribbon, a vector-field can be defined. Observing a line drawn by a pencil on an elastic tube one may easily be convinced about this. For an ideal tube with rotational symmetry the incremental twist equals the torsion of the curve, equation (1). In equation (1), r is a vector representation of the curve and the primes denote derivatives. Notice, that the above geometrical frame may be different from the physical frame imposed by the backbone itself due to additional twist of the physical backbone.

$$\tau = \frac{\vec{r}' \times \vec{r}'' \cdot \vec{r}'''}{|\vec{r}' \times \vec{r}''|^2} \qquad (1)$$

Twist excitations of the backbone will exist with a collective long range twist pattern. Such collective excitations are twist modes denoted twistons. Solitons may also exist as a pair of solitons can have a relatively low creation energy. However, note that such pairs do not destroy the long range order of the twistons, as a pair of solitons consists of an equal amount of clockwise and counterclockwise twist. The twistons that are present will depend on the boundary conditions at the two ends.

The basic reason for backbone of proteins to obey such winding property can be addressed in the two conjectures:

(a) The path of the segments of the polypeptide chain does not trace out unnecessarily complicated motions.

(b) The backbone does not rotate unnecessary.

The physical reason for the conjectures are that proteins do not fold in vacuum but rather in a viscous aqueous medium. Often they also interact with carbohydrates, other proteins and membranes.

The twistons are long range collective excitations over an entire protein folding domain. The polypeptide backbone will begin to bend at a certain amplitude of the local twist. The twist mode will involve non-zero values for the dihedral angle ν and therefore be rather stiff. The characteristic time scale involved can be much shorter than the characteristic time associated with the random motion of the unfolded backbone.

In general a change in the dihedral angles, φ and ψ will lead to a change in the path of the backbone. In contrast, a change in the twist maintain the path of the backbone. A twist mode therefore involves strained chemical bonds. However, the dihedral rotations $\psi_{i-1}$ and $\phi_i$ are almost coaxial. A rotation, and counter rotation of this kind, does not have significant long range implication for the twist of the backbone and thus does not interfere with long wavelength twist modes.

Resonator driven transition

The phase transformation of a protein from the unfolded structure to the folded structure is initiated by excitations of long wavelength twistons of the backbone which become unstable in favour of curvature. The nature of the transition may be characterized as being catastrophic rather than entropic. Thus, the primary reason for the transition is not a change in entropy. A twist mode is pumped to a higher and higher level occupancy (amplitude). A resonator is responsible for this pumping of the twist mode. The resonator must continuously be re-energized as is the case e.g. for thermal fluctuations by contact with a thermal bath. Almost literately, the initial folding of the protein can be thought as being analogous to the famous collapse of The Tacoma Narrows Bridge in Seattle, 1940. Twist modes of the bridge are excited by strong winds. Eventually, the amplitude of the twist modes becomes so large that the bridge fractures. The bridge did not have the option, that proteins do, to form folded structures.

A number of unique features follow from the scenario of a pumped transition. The resonance would be sensitive to the length of the polypeptide chain. This is consistent with protein folding domains all being of roughly the same length. For example, insulin is synthesized as a single chain which is folded before it is cleaved into its constituents being 21 and 30 amino acids long. Carbohydrates with large masses can define folding domains by constraining the twist modes. The part of the protein which would first begin to fold will depend on the twist mode, and on the detailed location of the different amino acids (the bridge broke at about the ¼ point—corresponding to maximum torsion). This means that the protein folding path to a large extend is deterministic and that folding can be a fast process.

Signal peptides

Secretory proteins are synthesized with a signal-peptide in the N-terminal of the polypeptide chain, as well as a possible propeptide. The signal peptide allows for the transfer of the polypeptide chain through membrane barriers. One possible hypothesis is that the signal-peptide are docking into membrane materials and thereby constraining the twist modes. After the initialization of the protein folding the signal peptide (and propeptide) is cleaved off. Clearly, for protein folding under such circumstances the winding (linking number) must be preserved in accordance with the method of the invention. More speculative, it is possible that during the docking of the signal peptide into the membrane it works as a mechanical screw and thereby promotes protein folding by initiating winding.

Aqueous media

Many proteins are known to fold and refold in an aqueous medium. The interaction with the media leads to dispersion which naturally must be minimized, i.e., the area of the surface spanned by all the intermediate states of the protein folding must be kept small. This leads to a nearly conserved linking number. Domains are segments of the polypeptide chain which folds under topological constraints as if each was a separate protein. Domains, which are empirical identified in proteins can either be of this kind, or an integer fraction hereof due to the symmetry of the responsible twiston.

Eigenfrequencies

The eigenfrequency of the polypeptide backbone twist modes can be estimated in the following way. An upper limit for the energy stored in a twist mode is estimated by considering the energies of the chemical bonds of the backbone. A rotation of π/2 of one bond is estimated to correspond to about 1 eV/Å, in accordance with typical bond energies. Hence, the torsion constant per inverse unit length, y is limited to about 0.4 eV/Å. The moment of inertia per unit length, i, of the backbone is about 100 a.u.Å, depending on the degree to which the side-chains are involved in the twisting. The eigenfrequency can be estimated to $$\nu = \frac{1}{2\pi L} \sqrt{\frac{y}{i}} \qquad (2)$$

where L is the length of the backbone. For a typical folding domain, e.g. 100 amino acids, L is about 380 Å, and the cyclic frequency ν becomes about 2.6 GHz. This frequency corresponds to typical vibrational (and rotational) frequencies of chemical bonds. It is only a rough estimate, but, the result is not very sensitive to the numbers chosen for y and i as they enter under the square-root in the equation.

The fact that the eigenfrequency of the twist mode may be as high as values typical for excitations of chemical bonds and structures (vibrations and rotations), agrees with a resonator that is present in the protein or the cell. The frequency ν scales inversely with the length of the backbone and resonance will not occur before a sufficiently long polypeptide chain has been synthesized in order to facilitate approximate frequency match. This explains why short polypeptide chains, such as the ones appearing in insulin, are folded when connected to form a longer chain. Pausing in the ribosome process may simply be a reflection of the variation in folding efficiency as a function of polypeptide length.

Consider the simplified case of a continuous isotropic model with the potential energy:

$$E_{pot} = \frac{1}{2}\int k_\tau \tau^2(l) + k_\kappa \kappa^2(l) dl$$

where $\tau$ is the torsion, $\kappa$ the curvature, and $k_\tau$, $k_\kappa$ the torsion and curvature elastic constants, respectively. Curvature is given by the space geometry of the backbone, torsion is given by a combination of space geometry and additional wringing. A wring state is stable when, differentially, a twisted line is stable against the formation of curvature preventing the formation of a helical line (screw line). The condition for stability is obtained after differentiating twice:

$$2k_\tau < k_\kappa$$

Molecular systems are not linear as the effective torsion and curvature constants change with the magnitude of the torsion and curvature variables. It is consequently necessary to consider the following three possible cases:

A: The above inequality is not valid. In this case the chain molecule will not sustain a wring mode.

B: The above inequality is valid for small amplitudes of the wring modes, but not for larger. In this case there is an amplitude of the wring mode, where a phase transformation takes place where the chain molecule changes its conformation.

C: The above inequality is valid for all amplitudes of the wring state that are biologically interesting. In this case the phase transformation that allows for structure formation in biomolecules, such as for example protein folding will not take place. On the contrary, excitation of wring modes will enforce a tendency to straighten the chain molecule, in the case of proteins to spontaneous denaturation.

The second case (B) is relevant for protein folding. It also shows that folded proteins maintain a standing pattern of wring oscillations. This pattern forms the basis for certain types of biological communications as docking on one side of a protein have global effect on the standing wring pattern. It also shows that denaturation can take place to either phase one (A), cold denaturation, or to phase three (C) hot denaturation. Further that it is not possible to go continuously form cold denaturation to hot denaturation with out a thermodynamic change.

Hydrolysis

It seems paradoxical that electromagnetic energy deposited in DNA and protein can be concentrated and focused in such a way that the energy subsequently can be released by the breaking of a single/double strand. The topological wring modes described herein can explain this. Before the breaking of the bond the energy of the wring mode is distributed along the chain molecule. Locally the angular strain can lead to conformational changes of the DNA or protein and eventually to breaking of a bond. This is the underlying symmetry breaking process that changes the energy distribution from being more or less evenly distributed to become concentrated in essentially a single bond before leading to the subsequent breaking.

Experimental Section

Description of various experimental techniques for measuring the structural changes in chain molecules during application of resonance driven effects.

It is important that the experimental techniques can detect changes in the structure of the chain molecules especially when they are strongly diluted in a solution and in a wide temperature and pressure range. The detection is focused on refolding experiments, and the issue is to what degree the tested chain molecules will undergo structural changes by application of an external modification. It is important that the methods are applicable even for solutions having a low concentration of the chain molecule. In the case of proteins it is preferred that the concentration is low, around or less than 1%, in order to reduce the tendency for unfolded chains to agglomerate.

Furthermore, it is important that the experimental setup for detection of the structural changes of the chain molecules can accommodate an in-situ application of apparatus for the external modifications such as microwave generators and the monitoring of their effects.

The experimental techniques for detection of the structure of the chain molecules in question can be divided into two categories:

1. Hydraulic measurements
2. Spectroscopic measurements

1. Hydraulic techniques, e.g. measurement of viscosity and sedimentation coefficients 1.a. Methods for measuring viscosity The specific viscosity of a liquid is dependent on the shape of the constituting molecules and their physical interactions. Usually the viscosity is found by measuring the torque that the liquid will assert on a rotating object in the liquid. Ordinarily, such rheometers are not sensitive enough for measuring strongly diluted chain molecules in a water solution. But instruments can be modified to also include a stronger friction, by expanding the rotating object and thus increasing the sensitivity to even minute concentrations of the substance. The rheometer can easily accommodate radiation generators and can be operated in a wide range of temperatures.

Modified rheometer setup

The rheometer block of a commercially available rheometer (DV-111 manufactured by Brookfield Instruments, M.A., U.S.A.) is placed in an automatic adjustable thermobath. The standard rotatable block of the rheometer is replaced with a cylindrical block consisting of a non-conducting material having an inner diameter of 10 mm and an outer diameter of 26.25 mm, enlarged with respect to the outer diameter (25.0 mm) of the standard UL-adaptor. (Rotatable blocks having an outer diameter between 2.5 mm and about 0.5 mm smaller than the inner diameter of the rheometer chamber show improved sensitivity over the standard setup due to the friction contribution to the rheometer output). A co-axial connector is fitted to the bottom part of the rheometer chamber and an inner metallic cylinder is connected to the connector whereby the inner cylinder and the inner surface of the rheometer chamber forms a co-axial electromagnetic resonator cavity with an approximately impedance match to the microwave generator electronics. An electromagnetic wave generator (8620 A manufactured by Hewlett-Packard, U.S.A.) is connected to the connector. The rotating cylindrical block is connected to the rheometer monitor through a stiff string in which it is suspended.

1.b. Methods for measuring the sedimentation coefficient

The measurement of the sedimentation coefficient is performed with an ultra centrifuge originally intended for molecular weight measurements. In such an experiment a rotor is spinning at a velocity of e.g. 100.000 revolutions/min. The boundary between the solution and the solute-free solvent moves away from the centre of rotation at a rate which is proportional to the sedimentation coefficient. This coefficient is also proportional to the molecular weight, the densities and the friction coefficient. The friction coefficient depends on the departure of the protein from spherical shape. Therefore the overall shape of a chain molecule can be found if the densities, molecular weight and the velocity of the boundary between the solution and the solvent can be measured. The method is generally not accurate enough for water solutions, but can be useful when other solvent systems are used.

Modified ultra-centrifuge

Around the centrifuge is built a conducting cavity, which allows for an electromagnetic microwave field to be present at the sample.

2. Spectroscopic measurements, e.g. absorption spectroscopy and emission spectroscopy Spectroscopic methods are basically divided into absorption spectroscopy, e.g. UV absorption spectroscopy, difference spectroscopy, and NMR spectroscopy, and emission spectroscopy e.g. fluorescence measurements. In both cases ORD (Optical rotatory dispersion) and CD (Circular dichroism) polarization measurements can be applied.

2.a. Optical rotatory dispersion, ORD, experiments

The optical rotation is a measurement of the chirality of the chain molecules. Thus, the rotation of the optical plane is dependent on the formation of ordered structures in the native tertiary state of the chain molecule. A transparent polished glass cell containing the chain molecule in solution is inserted in the apparatus and polarized light is passed through the glass cell. Water from an automatic adjustable thermobath flows through the outer part of the glass cell in order to maintain a predetermined temperature. The rotation of the light passing through the glass cell is monitored in order to determine whether the chain molecule is in a folded or unfolded state. The drawback of this experiment is that only the chain molecules in an almost transparent solution can be analyzed. All the applications and usage of ORD are valid for CD techniques as well.

Modified polarimeter

A polarimeter (141 manufactured by Perkin-Elmer, Germany) is used. The standard glass cell of the polarimeter need not to be modified as an electromagnetic cavity is build around it. Electromagnetic radiation is applied from a microwave radiation source via a wave guide or a co-axial cable. Alternatively the cell can be constructed to incorporate the use of electromagnetic radiation to optimize the cavity and its impedance match with the cable and source. In this case care must be taken to use transparent windows of a sufficient optical quality and flatness, e.g. optically polished quarts windows. A typical size for the length is about 4 cm; one must assure that the efficiency of the cuvette is reasonable at the frequency used; this involves an adjustment of the dimensions of the cuvette. One common mode of operation is with the electric-field transverse to the path of the light.

2.b. Fluorescence measurements

The fluorescence setup makes use of an excitation and emission monochromator to produce emission spectra of wavelength distribution from the emitted light from excited states. The emission spectra contain characteristic signals from different functional groups, e.g. side-chain indoles of tryptophanes in proteins. The signals are sensitive to the environment of the functional groups, and will therefore make a distinction between the native and denatured states of the chain molecule. The sample to be examined is inserted into a glass container. Such apparatus is commercially available.

The advantage of this techniques is that it is very sensitive to the environment and thus can be used for analyzing e.g. proteins in a special environment of e.g. lipid membranes or ligand binding sites in proteins.

Modified fluorescence detector

Microwaves can be applied from a co-axial cable into a electromagnetic cavity build around the glass tube. The electromagnetic cavity is essentially consisting of the metal housing of the apparatus.

2.c. Nuclear magnetic resonance, NMR

NMR studies allow for a more comprehensive analysis of the geometry of the molecule. In NMR spectroscopy, the band separations in the absorption spectrum are due to changes in the spin of the nucleus and are very narrow and distinct. They arise from spin transitions. Usually, the width of an absorption band is dependent on the rate of the processes in the molecular system.

NMR spectroscopy can provide data of rapid conformational changes. This allows for studying of collective vibrational changes of the molecule and it gives a unique possibility for studying the consequences of applying microwave radiation. The application of microwave radiation is rather straight forward and the reward is a more detailed picture of the structural changes as NMR can provide a better time resolution in the analysis of the phenomenon. The magnet of the NMR apparatus contains large magnetic fields and the application of microwave radiation must therefore be feed through properly constructed wave guides. The microwave signal is superimposed on the radio frequency (RF) signals already present in the system. Alternatively, it is possible to modify the NMR apparatus to include slightly higher frequencies than those normally used for structure determination, and thereby enabling excitation of the twiston modes at their resonance frequencies.

A confirmation of the existence of wringon's can be made using an NMR instrument and studying the dynamical behaviour of proteins. Further, by applying and scanning the frequency range of the applied radiation during a recording of the NMR-signals it is possible to identify the structural changes associated with wringons and with artificially stimulated wringons.

2.d. Small angle scattering

Small angle X-ray or neutron scattering are important means for getting structural information about proteins in solution. Specifically, the predictions of the phase diagram and of the dynamical stabilization of the secondary structures can be confirmed in comparative studies of cold and hot denaturated phases.

General considerations

All the mentioned techniques for bio-molecular structure determination can be implemented or improved by adding wave generators and wave guides so that external radiation can be exerted on the bio-molecules causing fundamental topological changes in their structure. Especially, what concerns application of microwave radiation such an addition will cause very little disturbances in the spectroscopy detectors due to the statistical nature of bosons that leads to the principle of superposition. Of course the use of microwaves requires special attention to the materials and design of the apparatus such as metallic cavities and use of plastic and other non-conducting materials for constructions inside the cavities.

Todays detectors of biomolecular structures are stretched to the technical limits in order to achieve a resolution down to a few Ångströms. It is practically impossible to interfere physically and cause a desired change in the molecular system under detection other than random temperature effects and chemical reactions that usually will have little effect on the structure of the biomolecule other than breaking up the structure. However, by applying external radiation in a specific frequency range profound change in the topological structure of the bio-molecules can be achieved. The route to a desired conformation can be either directly toward a native state or by creation of an intermitted dis-aggregational state.

In order to obtain a uniform group of chain molecules, when structure determination of chain molecules is preformed, stimulation with high frequency energy can be utilized either continuously or intermittently.

EXAMPLE 1

β-Lacto globulin (from bovine milk)

The three-dimensional structure of the protein in its folded form is known (Brookhaven Protein Data Bank). The protein has a barrel like structure consisting of β-sheets. The protein is useful to demonstrate the effect of the applied high frequency energy because it can undergo a transition from an unfolded state to a folded state under moderate conditions (10° C. (unfolded) to 25° C. (folded) and at a temperature between 25° C. (folded) to 90° C. (unfolded)) and because its native three-dimensional structure can easily be distinguishing from its unfolded (denatured) three-dimensional structure. [Often proteins have well-defined intermediate states, as well. Hence, β-lacto globulin is not in all aspects a prototypical example of a protein.]

Viscosity/friction measurements (10–25° C.)

Five samples are prepared:
i pure water
ii urea solution (8 M)
iii native (folded) β-lacto globulin (1 mg/ml in 0.3 M KCl) and HCl to pH 1.5
iv denatured (unfolded) β-lacto globulin (1 mg/ml in 8 M urea)
v unstable β-lacto globulin (1 mg/ml, 0.3 M KCl, and HCl to pH 1.5), 4 M urea; unfolded at 10° C. and folded at around 20° C.)

The viscosity/friction of each of the samples are measured for temperatures in the range 10 to 30° C. (step size 1° C.) in the modified rheometer described herein. The viscosity/friction values for sample iii and iv are corrected for the urea and water contribution and the contribution of the folded protein and the unfolded protein, respectively, is obtained. The ratio between the folded and the unfolded form at different temperatures is calculated for sample v.

The rheometer is fully able to distinguish between the native and denatured states the latter having a viscosity being about twice as big as that of the native state. The total protein contribution is in the range of 1–20% depending on concentration and protein. Interestingly, the unstable sample undergoes a phase transition between 10° C. and 22° C. When microwave radiation is applied at a fixed temperature around the-phase transition (approx. 18° C.) the viscosity is decreased, just as would have been the case if the temperature was increased. The protein is apparently changing from the unfolded state to the folded state. In the temperature cycles where the temperature is gradually lowered, the effect of temperature and microwave can be unambiguously separated.

EXAMPLE 2

β-Lacto globulin (from bovine milk)
Optical rotatory dispersion measurements (10–25° C.)

The modified polarimeter described herein is used. Samples iii–v from Example 1 are used. The optical rotation for each sample is measured for temperatures in the range from 10 to 25° C. The ratio between the folded and the unfolded protein at different temperatures is calculated for sample v.

This instrument gives a clear difference in signal for the folded and unfolded structure. When microwave radiation is applied at a fixed temperature, e.g. 18° C., the viscosity is decreased, just as would have been the case if the temperature was increased. The protein is apparently changing from the unfolded state to the folded state. In the temperature cycles where the temperature is gradually lowered, the effect of temperature and microwave can be unambiguously separated.

EXAMPLE 3

Rhodanese (from bovine liver)

The three-dimensional structure of rhodanese is not known with the same accuracy as β-lacto globulin. The protein is very unstable and can not refold unless micelles/lipids are added. Special care has to be taken in order to avoid agglomeration e.g. by using strongly diluted solutions.

a. Viscosity/friction measurements

The measurements are performed using the modified rheometer described herein. Similar samples as prepared in Example 1.a. are used except that a micelles forming agent (e.g. lauryl maltoside) and a disulphide redox buffer (e.g. reduced/oxidized β-mercapto-ethanol) are added to each sample.

EXAMPLE 4

Rhodanese (from bovine liver)
a. Fluorescence measurements

The measurements are performed using the modified fluorescence detector described herein. Similar samples as prepared in Example 3.a. above are used.

EXAMPLE 5

Lysozyme (from hen eggs white)

It is not easy to analyze because it comprises four disulphide bridges. However, lysozyme is very cheap and it is very well described with respect to refolding processes and therefore it is a good target for an analysis of the impact of using the twiston assisted protein folding technique. The formation and breaking of the disulphide bonds during the experiments can be overcome by adding a disulphide redox buffer (e.g. reduced/oxidized β-mercapto-ethanol).

a. Viscosity/friction measurements

The measurements are performed using the modified rheometer described herein. Similar samples as prepared in Example 1.a. are used except that a disulphide redox buffer (e.g. 2.0 mM/0.2 mM reduced/oxidized glutathione) is added to each sample.

EXAMPLE 6

Lysozyme (from hen eggs white)
a. Optical rotatory dispersion measurements

The measurement are performed using the modified rheometer described herein. Similar samples as prepared in Example 5.a. above are used.

The phase diagram of protein folding/denaturing can be measured by a polarimeter connected to a thermobath where the temperature and pH can be measured. A protein solution with urea in an acidic buffer system with a specific pH-value is held in a cuvette in the polarimeter.

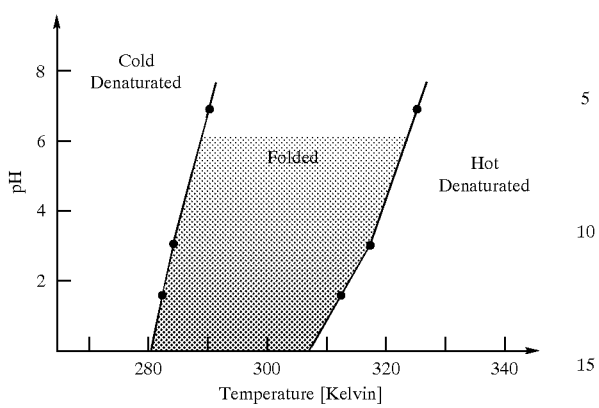

Temperature [Kelvin]

The figure shows the phase diagram for beta-lactoglobulin in an acidic 4 molar urea solution. Cold-denaturated, folded and hot-denaturated protein are present. The phase diagram has been determined from the optical rotation data recorded by the polarimeter in refolding experiments. This experiment confirms the prediction made from the consideration of the elastic constants, namely that it is not possibly to go from cold to hot denatured protein without passing thermodynamic borders (corresponding to the case A and C described above). A unique feature of the wringon model for proteins.

The knowledge of the phase diagram is important for understanding how to reach the folded or unfolded state of a protein. Often attempt to fold proteins by going from phase A to phase B and attempts to fold proteins going form phase C to phase B does not lead to the same results. It can therefore be learned from the theory and experiment presented above that one way of folding proteins which display folding difficulties is to form a solution corresponding to the thermodynamical phase A (cold denaturation) and then change one or more parameters such as temperature, pH, denaturant, etc. to change the solution into a phase B solution. Another important feature of the phase diagram is the possibility to modify the stability of proteins by changing external parameters such as for example the pH. An embodiment of this invention is to treat prion caused diseases where the advancement of the diseases can be slowed by medication that changes the overall parameters as discussed above and thereby slows down the structural changes of the involved proteins before the unwanted conformation is reached.

Experiments demonstrating wringon effects in catalyzed processes

1. Enhancement of the process that converts sugar to alcohol. Within a yeast culture during e.g. beverages process, ethanol is produced from acetaldehyde during anaerobic fermentation of sugar. The rate of fermentation depends on the temperature. For beverages the desired temperature when considering the taste of the product is lower than the desired temperature when considering production rate. One embodiment of the present invention is to improve fermentation rates by use of electromagnetic radiation; in the case of beverages products at the desired temperature for taste. Microwave is applied in a fermentation tank during the process. When desired, the temperature can be controlled by a refrigeration unit and the process can be monitored by standard means such as a pH measurement.

2. Enhancement of enzymatic protease activity by studying for example the α-lytic protease activity during refolding experiments with applied microwave radiation and with/without propeptide. The α-lytic protease can not refold successfully unless a propeptide or similar peptides are added to the solution. Alternatively one can add a properly designed molecular resonator or apply microwave radiation to the solution containing the denatured protein. The protease attain its enzymatic function when it has regained its folded native structure. There are many other cases of enzyme production that similarly need molecular resonators and/or externally added energy for the involved proteins to attain the folded functional state. Examples are insulin, concanavalin etc. i.e. microwave radiation can be beneficial to the enzymatic functionality.

3. Peroxidase blood test with varying pH values and during applied microwave irradiation. Very small traces of blood, e.g. human, bovine or porcine, in a liquid such as urine can be measured by the use of peroxidase that is an oxidoreductase which catalyses a reaction involving reduction of hydrogen peroxide.

Experiments demonstrating wringon effects in ligand binding processes

4. Binding of cytochrome B5 (and other heme binding proteins) to a hemegroup which can be monitored by observing a colour change in the protein. The protein becomes red when a heme group is binding to it. It is therefore easy to evaluate the degree of binding affinity (and in refolding experiments, the degree of folding) when microwave radiation is applied by using spectrophotometry.

5. Binding of antibody to antigen. It is also envisaged that this binding can be altered by applying microwave radiation. There is here, as well as for some of the cases above, toolkits that can make a monitoring of the process easy. In some cases it is actually expected that microwave radiation can diminish the binding affinity of antibodies to antigens and that can be easily monitored.

6. Crystallization experiments to test the hypothesis that microwaves and initiation of wring excitations can alter the degree of protein aggregation. There should be an upper limit of the domain size for the formation of crystals corresponding to the wave length of the wring modes.

Experiments demonstrating wringon effects in signal transduction processes

7. Experiments with bacterio-rhodopsin to see if microwave can alter the communication path. The light harvesting protein can be examined with respect to the dramatic hue on the surface of samples of the protein material. One example is studying the efficiency of solid state compound device which incorporates a film of the protein. The efficiency of the device is monitored with and without the simultaneous application of microwaves.

8. Experiments with G-binding proteins. Protein receptor fixed in an artificial membrane could constitute a good lab kit for future signal experiments.

9. Transfer of signal in structural damaged neuro-cells with amyloid aggregation that can be restored partly by applying microwave radiation.

Experiments with test set testing for enzymatic activity preferred with colour indication, e.g. a pregnancy test or other over the disk test such as the Boehringer Mannheim Test 5 L (pH, protein, glucose, ketones, blood). The time for identical test to indicate a result is studied with as well as without exposure to electromagnetic radiation of low intensity with no considerable heating of the test set. This is done in a special constructed cavity with a glass, or a metal wire window which is constructed to have a reasonable impedance match with the radiation source and a reasonable value, i.e. generator and cable. In special cases that are not very critical, half of the tests can be placed in a conventional, e.g. commercial, microwave oven. One particular embodiment of the above is a cylindrical box, diameter about 10 cm and height about 3 cm in which the inner wire in the coaxial cable connecting a microwave generator forms a loop antenna within the box. The box is constructed with variable height in order to improve the efficiency of the setup. Similarly, the symmetry of the box can be broken by an inner cylinder which does not have the full height of the box. In the narrow gap a high field can therefore be obtained and the result of the electromagnetic radiation more easily be observed. At the top of the cylinder a wire grid with wire spacing of about 1 mm is place. This allows for the direct observation of the phenomenon.

One way of understanding the usefulness of a molecular resonator is by the use of computer simulations where the standing wring patterns are studied on a protein in connection with and without the resonator, damper or other ligand. As special case of such computer calculations is the use of higher dimensional lattice representations of the polypeptide chain which include orientation, e.g. five and six dimensional space.

What is claimed is:

1. A method for changing the functionality of the three-dimensional structure of one or more chain molecules each having a one-dimensional primary structure comprising a backbone the predominant number of bonds of which are non-coaxial or rotationally non-symmetrical, or of aggregates of such molecules, the method comprising applying high frequency energy having maximum energy at a frequency in the range of 0.01–100 GHz to a fluid system containing such chain molecules under conditions with respect to parameters involving wavelength, amplitude and duration which will initiate a change of the three-dimensional structure which is different from the starting functionality of the three-dimensional structure, provided that substantially no decomposition of the backbone of said chain molecule is caused by the application of the high frequency energy.

2. A method according to claim 1, wherein the high frequency energy source is an external energy source.

3. A method according to claim 1, wherein, when the temperature of said fluid system is above 50° C., the temperature increase due to the application of the high frequency energy is lower than 5° C.

4. A method according to claim 1, wherein no decomposition of the backbone of the chain molecule is caused by the application of the high frequency energy.

5. A method according to claim 1, said method comprising applying high frequency energy to the fluid system comprising said selected chain molecule;

intermittently or continuously monitoring the effect of the applied high frequency energy by monitoring the change in three-dimensional structure of said selected chain molecule; and optionally adjusting the conditions with respect to parameters involving frequency, amplitude, and duration of the high frequency to enhance said effect.

6. A method according to claim 1, wherein the desired change in the three-dimensional structure of the chain molecule is assessed by measurement of the biological effect of the chain molecule.

7. A method according to claim 1, wherein the energy is applied at a frequency at which resonance of a collective twist mode can be obtained.

8. A method according to claim 7, wherein the frequency is from 1/10 to 10 times the resonance frequency of the twist mode.

9. A method according to claim 8, wherein the frequency of the applied energy is in the range of 0.1 to 10 GHz.

10. A method according to claim 8, wherein the band width of the applied high frequency energy at half maximum is at the most 0.5 GHz.

11. The method of claim 10 where said band width is at most 0.1 GHz.

12. A method according to claim 7, wherein the excitation of the twist mode is performed by applying electromagnetic radiation.

13. A method according to claim 12, wherein the energy is applied by using at least one microwave resonator.

14. A method according to claim 1, wherein the energy is applied by using a circuit which generates broad-spectrum high frequency radiation, or a device which generates broad-spectrum high frequency vibrations.

15. A method according to claim 1, wherein the application of high frequency energy is performed intermittently and the amplitude of the high frequency energy is gradually decreased.

16. A method according to claim 1, wherein the fluid system further comprises a disulphide redox system.

17. A method according to claim 1, wherein the original three-dimensional structure represents a first folded state of the chain molecule and the resulting three-dimensional structure represents a second folded state of the chain molecule, the fuctionality of said first folded states being different from the functionality of said second folded state.

18. A method according to claim 1, wherein the original three-dimensional structure represents an unfolded state of the chain molecule and the resulting three-dimensional structure represents a folded state of the chain molecule.

19. A method according to claim 1, wherein the initial three-dimensional structure represents a folded state of the chain molecule and the resulting three-dimensional structure represents an unfolded state of the chain molecule.

20. A method according to claim 19, comprising:

disintegrating the aggregates by applying high frequency energy from an external energy source;

optionally adding a disulphide redox system to the fluid system; and applying high frequency energy to the fluid system correspond to the resonance frequency, v, of the twist mode of the chain molecule, said resonance frequency being estimated as $$v = \frac{1}{2\pi L} \sqrt{\frac{y}{i}}$$

where y is the torsion energy per inverse unit length, i is the moment of inertia per unit length, and L is the length of the backbone of the chain.

21. A method according to claim 1, wherein the fluid system further comprises one or more solid phase support particle(s), and where the chain molecule is attached to said solid phase support at least during the application of high frequency energy.

22. A method according to claim 21, wherein the chain molecule is a polypeptide or a protein immobilized on a solid phase support used for solid phase peptide synthesis.

23. A method according to claim 22, wherein a disulphide redox system is present in or added to the fluid system comprising the immobilized polypeptide or protein.

24. A method according to claim 1, wherein the chain molecule is a molecule selected from the group consisting of:

natural proteins;

tailored proteins;

genomic chain molecules; artificial genomic chain molecules;

carbohydrates; and synthetic organic polymers.

25. A method according to claim 24, wherein the chain molecule is a natural protein or a tailored protein.

26. A method according to claim 24, wherein the chain molecule is an antibody.

27. A method according to claim 1, wherein the aggregate of chain molecules is selected from the group consisting of:

oligomers of chain molecules;

protein/receptor systems;

inclusion bodies; and membranes comprising chain molecules or oligomers thereof.

28. A method according to claim 27, wherein the aggregate comprising the chain molecules is an inclusion body.

29. The method of claim 1 wherein the frequency of the applied energy is in the range of 1 to 5 GHz.

30. The method of claim 1 where the applied frequency is different from the resonant frequency.

31. A method for the preparation of a desired polypeptide having a desired three-dimensional structure, the method comprising:

preparing a fluid system comprising a polypeptide comprising a sequence part identical to the sequence of the desired polypeptide, said polypeptide further comprising a sequence part or sequence parts which will ensure that the entire polypeptide has a collective twist mode which when stimulated will result in said desired three-dimensional structure of said sequence part identical to the sequence of the desired polypeptide;

exciting said collective twist mode, and thereby changing the functionality of the three-dimensional structure of said polypeptide by the method of claim 1 under conditions with respect to source and parameters involving frequency, amplitude and duration which will initiate a structural change to result in the desired three-dimensional structure of the desired polypeptide, provided that substantially no decomposition of the backbone of the desired polypeptide is caused when said excitation is performed by application of high frequency energy;

optionally forming one or more —S—S—bonds by using a disulphide redox agent; and cleaving the bond(s) of the polypeptide upstream and/or downstream of the desired polypeptide with substantially no alteration of the three-dimensional structure of the desired polypeptide.

32. A method for changing the functionality of the three-dimensional structure of one or more chain molecules each having a one-dimensional primary structure comprising a backbone, the predominant number of bonds of which are non-coaxial or rotationally non-symmetrical, or of aggregates of such molecules, the method comprising applying high frequency energy, said energy having a frequency which is from 1/10 to 10 times the estimated resonance frequency, ν, of the twist mode of the chain molecule, said resonance frequency being estimated as $$\nu = \frac{1}{2\pi L}\sqrt{\frac{y}{i}}$$

where y is the torsion energy per inverse unit length, i is the moment of inertia per unit length, and L is the length of the backbone of the chain, to a fluid system containing such chain molecules under conditions with respect to parameters involving wavelength, amplitude and duration which will initiate a change of the three-dimensional structure which is different from the starting functionality of the three-dimensional structure, provided that substantially no decomposition of the backbone of said chain molecule is caused by the application of the high frequency energy.

33. The method of claim 32 where "y" is assigned a value of 0.4 ev/angstrom and "i" a value of 100 a.u. angstrom.

* * * * *